US008343500B2

(12) United States Patent
Wraith et al.

(10) Patent No.: US 8,343,500 B2
(45) Date of Patent: *Jan. 1, 2013

(54) PEPTIDE COMPOSITION

(75) Inventors: David Cameron Wraith, Bristol (GB); Heather Barbara Streeter, Bristol (GB)

(73) Assignee: Apitope Technology (Bristol) Limited, Bristol (GB)

( * ) Notice: Subject to any disclaimer, the term of this patent is extended or adjusted under 35 U.S.C. 154(b) by 931 days.

This patent is subject to a terminal disclaimer.

(21) Appl. No.: 11/979,224

(22) Filed: Oct. 31, 2007

(65) Prior Publication Data

US 2008/0200368 A1     Aug. 21, 2008

Related U.S. Application Data

(63) Continuation-in-part of application No. 10/362,264, filed on Jun. 5, 2003, which is a continuation of application No. PCT/GB01/03702, filed on Aug. 17, 2001.

(30) Foreign Application Priority Data

Aug. 21, 2000  (GB) .................................. 0020618.5
Jun. 14, 2001  (GB) .................................. 0114547.3

(51) Int. Cl.
| | |
|---|---|
| A61K 38/04 | (2006.01) |
| A61K 38/00 | (2006.01) |
| A61K 39/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |

(52) U.S. Cl. ...................... 424/185.1; 530/300; 530/326

(58) Field of Classification Search ......................... None
See application file for complete search history.

(56) References Cited

U.S. PATENT DOCUMENTS

| | | | |
|---|---|---|---|
| 5,593,698 A | 1/1997 | Weiner et al. | |
| 5,817,629 A | 10/1998 | Warren et al. | |
| 5,858,980 A | 1/1999 | Weiner et al. | |
| 5,989,565 A | 11/1999 | Storkus et al. | |
| 6,379,670 B1 * | 4/2002 | Gaur et al. ................. | 424/184.1 |

FOREIGN PATENT DOCUMENTS

| | | |
|---|---|---|
| EP | 0286447 | 10/1988 |
| WO | WO 88/10120 | 12/1988 |
| WO | WO-95/31997 | 11/1995 |
| WO | WO-9616086 | 5/1996 |
| WO | WO-96/32957 | 10/1996 |
| WO | WO-98/13378 | 4/1998 |
| WO | WO-99/63945 | 12/1999 |
| WO | WO-00/11027 | 3/2000 |
| WO | WO-00/42863 | 7/2000 |
| WO | WO-03/064464 | 8/2003 |

OTHER PUBLICATIONS

Bielekova et al. 'Encephalitogenic potential of the myelin basic protein peptide (amino acids 83-99) in multiple sclerosis: Results of a phase II clinical trial with an altered peptide ligand.' Nature Medicine. 6(10):1167-1175, 2000.*
Fairchild et al., "An autoantigenic T cell epitope forms unstable complexes with class II MHC: a novel route for escape from tolerance Induction", International Immunology, Oxford University Press, 5(9):1151-1158 (1993).
Akdis, et al, "Role of Interleukin 10 in Specific Immunotherapy," American Society for-Clinical Investigation, Inc., vol. 102, No. 1, pp. 98-106 (Jul. 1998).
Anderton, et al., "Hierarchy in the Ability of T Cell Epitopes to Induce Peripheral Tolerance to Antigens From Myelin," Eur. J. Immunol., vol. 28, pp. 1251-1261 (1998).
Anderton, et al., "Influence of a Dominant Cryptic Epitope on Autoimmune T Cell Tolerance," Nature Immunology, vol. 3(2), pp. 175-181 (2002).
Anderton, et al., "Mechanisms of Central and Peripheral T-cell Tolerance: Lessons From Experimental Models of Multiple Sclerosis," Immunological Reviews, vol. 169, pp. 123-137 (1999).
Burkhart, et al., "Peptide-Induced T Cell Regulation of Experimental Autoimmune Encephalomyelitis: A Role for Interleukin-IL10," International Immunology, vol. 11, pp. 1625-1634 (1999).
Carnegie, Biochem, J., vol. 123, pp. 57-67 (1971).
Cherian, et al., Touch Briefings Bioprocessing & Biopartnering, pp. 20-21 (Jun. 2006).
Chou, et al., J. Neurochem., vol. 46, pp. 47-53 (1986).
DeGraaf, K., et al., "Allelic Variations in Rate MHC Class II Binding of Myelin Basic Protein Peptides Correlate with Encephalitogenicity," International Immunology, vol. 11, No. 122, pp. 1981-1987.

(Continued)

*Primary Examiner* — Nora Rooney
(74) *Attorney, Agent, or Firm* — Marshall, Gerstein & Borun LLP

(57) ABSTRACT

There is provided a method for selecting a tolerogenic peptide by selecting a peptide which is capable of binding to an MHC class I or II molecule without further processing. There is also provided a peptide selected by such a method and its use in a pharmaceutical composition and a method to treat and/or prevent a disease. The present invention also relates to a composition which comprises the following myelin basic protein (MBP) peptides: MBP 30-44; MBP 83-99; MBP 131-145; and MBP 140-154. The composition may be used to treat a disease, in particular multiple sclerosis and/or optical neuritis and the invention also relates to such uses and methods.

1 Claim, 26 Drawing Sheets

OTHER PUBLICATIONS

Diment, S., "Different Roles for Thirol and Aspartyl Proteases in Antigen Presentation of Ovalbumin," Journal of Immunology, vol. 145, No. 2, pp. 417-422 (1990).

Dunkley, et al., Biochem. J., vol. 141, pp. 243-255 (1974).

Eylar, et al., J. Biol. Chem., vol. 246, pp. 5770-5784 (1971).

Fairchild, et al., "The Nature of Cryptic Epitopes Within the Self-Antigen Myelin Basic Protein," International Immunology, vol. 8, pp. 1035-1043 (1996).

Gradehandt, G. and Ruede, E., "The Endolysomal Protease Cathepsin B Is Able to Process Conalbumin Fragments for Presentation to T Cells," Immunology, vol. 74, No. 3, pp. 393-398 (1991).

Hampl, J., et al., "In Vitro Processing of Insulin for Recognition of Murine T Cells Results in the Generation of a Chains With Free CysSH," Journal of Immunology, vol. 148, No. 9, pp. 2664-2671 (1992).

Jennings, IVD Technology Magazine, Parts 1 and 2 (1997).

Kamholz, et al., Proc. Natl. Acad. Sci., vol. 83, pp. 4962-4966 (1986).

Liu, et al., "Affinity for class II MHC determines the extent to which soluble peptides tolerize autoreactive T cells in naive andprimed adult mice—implications for autoimmunity," Informational Immunology, vol. 7, No. 8, pp. 1255-1263 (1995).

Liu, et al., "Low Avidity Recognition of Self-Antigen by T Cells Permits Escape From Central Tolerance," Immunity, vol. 3, pp. 407-415 (1995).

Martenson, Prog. Clin. Biol. Res., vol. 146, pp. 511-521 (1984).

Medveczky, et al., FEBS Letters, vol. 580, pp. 545-552 (2006).

Metzler and Wraith, "Inhibition of T Cell Responsiveness by Nasal Peptide Administration: Influence of the Thymus and Differential Recovery of T Cell-Dependent Functions," Immunology, vol. 97, pp. 257-263 (1999).

Muller, et al., Successful Immunotherapy with T-Cell Epitope Peptides of Bee Venom Phospholipase A2 Induces Specific T-Cell Anergy in Patients Allergic to Bee Venom, J. Allergy Clin. Immunol., pp. 747-754 (1998).

Najeme, et al., Brain Research Protocols, vol. 1, pp. 133-138 (1997).

Pette, M., et al., "Myelin Autoreactivity in Multiple Sclerosis: Recognition of Myelin Basic Protein in the Context of HLA-DDR2 Products by T Lymphocytes of Multiple-Sclerosis Patients and Healthy Donors," Poroc Natl. Acad. Sci. USA, vol. 87, pp. 7968-7972, Oct. 1990.

Pribyl, et al., Proc. Natl. Acad. Sci., USA, vol. 90, pp. 10695-10699 (1993).

Roth, et al., J. Neurosci. Res., vol. 17, pp. 321-328 (1987).

Rule 114(2) EPO Communication, Apitope Technology (Bristol) Limited, App. No. 06014901.0 (Dec. 13, 2007).

Santambrogio, et al., "Abundant empty class II MHC molecules on the surface of immature dendritic cells," PNAS, vol. 96, No. 26, pp. 15050-15055 (1999).

Segal, et al., J. Neuroimmunol., vol. 51, pp. 7-19 1994.

Vacchino, J. Immunology 166, pp. 6680-5 (2001).

Vogt, et al., "Ligand Motifs of Hla-DRB5*0101 and DRB1*1501 Molecules Delineated from Self-Peptides," Journal of Immunology, pp. 1665-1673 (1994).

Voskuhl, et al., Journal of Neuroimmunology, vol. 42, pp. 187-192 (1993).

Wicker, et al., "Naturally Processed T Cell Epitopes from Human Glutamic Acid Decarboxylase Identified Using Mice Transgenic for the Type 1 Diabetes-associated Human MHC Class II Allele, DRB1*0401," J. Clin. Invest., vol. 98, No. 11, pp. 2597-2603 (Dec. 1996).

Wucherpfennig, K., et al., "Recognition of the Immunodominant Myelin Basic Protein Peptide by Autoantibodies and HLA-DR2-restricted T Cell Clones from Multiple Sclerosis Patients," J. Clin. Invest., vol. 100, No. 5, pp. 1114-1122, Sep. 1997.

Deibler, et al., Preparative Biochemistry, 2:139-165 (1972).

Haines, et al., Human Mol. Genet. 7:1229-1234 (1998).

Lehmann, et al., Nature, 358:155-157 (1992).

Madsen, et al., Nature Genetics, 23:343-347 (1999).

Metzler and Wraith, Int. Immunol. 5:1159-1165 1993.

Nepom and Ehrlich, Ann. Rev. Immunol. 9:493-525 (1991).

Parker, K.C., et al., J. Immunol. 152:163-175 (1994).

Roberge, J.Y., et al., Science 269:202-204 (1995).

Summers, et al., Am. J. Pathol. 159:285-295 (2001).

Sundstedt, et al., J. Immunol., 170:1240-1248 (2003).

Viner, et al., Proc. Natl. Acad. Sci. 92:2214-2218 (1995).

Zamvil, et al., Nature, 317:355-8 (1985).

Bielekova, B. et al. "Encephalitogenic potential of the myelin basic protein peptide (amino acids 83-99) in multiple sclerosis: results of a phase II clinical trial with an altered peptide ligand," Nature Medicine, 6:10, 1167-1175 (Oct. 2000).

Hemmer, B. et al. "Human T-cell response to myelin basic protein peptide (83-99): Extensive heterogeneity in antigen recognition, function, and phenotype," Neurology, 49, 1116-1126 (1997).

Kappos, L. et al., "Induction of a non-encephalitogenic type 2 T helper-cell autoimmune response in multiple sclerosis after administration of an altered peptide ligand in a placebo-controlled, randomized phase II trial," Nature Medicine, 10, 1176-1182 (2000).

Kozovska, M. et al. "T cell recognition motifs of an immunodominant peptide of myelin basic protein in patients with multiple sclerosis: structural requirements and clinical implications," European Journal of Immunology, 28, 1894-1901 (1998).

Higgins et al., "Suppression of experimental autoimmune encephalomyelitis by oral administration of myelin basic protein and its fragments", J. Immunol., 140:440-445 (1988).

Janeway and Travers, "The Thymus and the Development of T Lymphocytes", Immunobiology, published Garland Publishing, pp. 6:1-6:2, 6:18-6:19, 6:25- 6:26 (1994).

Janeway and Travers, "Peptides presented by MHC class II molecules are generated in acidified intracellular vesicles", Immunobiology, published Garland Publishing, Figure 4:13. (1994).

Liblau et al., "T cell response to myelin basic protein epitopes in multiple sclerosis patients and healthy subjects", Eur. J. Immunol., 21:1391-1395 (1991).

Meinl et al., "Activation of a myelin basic protein-specific human T cell clone by antigen-presenting cells from rhesus monkeys", International Immunology, 7(9):1489-1495 (1995).

Pender et al., "A study of human T-cell lines generated from multiple sclerosis patients and controls by stimulation with peptides of myelin basic protein", Journal of Neuroimmunology, 70:65-74 (1996).

Sequence from human MBP Database SwissProt, Derwent (P02686), May 26, 2011.

\* cited by examiner

Response to MBP peptides in MS patients: 1st time point

| | MBP | 1 to 24 | 15-39 | 30-54 | 45-69 | 60-84 | 75-99 | 90-114 | 105-129 | 120-144 | 135-159 | 150-170 |
|---|---|---|---|---|---|---|---|---|---|---|---|---|
| MS 10 | + | + | - | - | - | - | - | - | - | - | - | - |
| MS 17 | + | + | - | + | - | - | - | - | - | - | - | - |
| MS 19 | - | - | - | - | - | - | - | - | + | - | - | - |
| MS 39 | + | + | + | - | - | - | - | + | - | - | + | - |
| MS 41 | + | + | + | + | - | - | + | + | + | + | - | + |
| MS 43 | + | - | + | + | - | - | + | - | - | + | - | - |
| MS 49 | + | + | - | - | - | - | - | - | + | - | - | + |
| MS 57 | + | - | - | + | - | - | + | + | - | - | + | + |
| MS 59 | + | - | - | + | + | - | + | + | + | + | + | + |
| MS 60 | + | - | - | - | - | - | - | - | - | - | - | + |
| MS 67 | + | - | - | - | - | - | - | - | - | - | - | - |
| MS 80 | + | - | - | - | - | - | - | - | - | - | - | - |

Response to MBP peptides in MS patients: 2nd time point

| | MBP | 1 to 24 | 15-39 | 30-54 | 45-69 | 60-84 | 75-99 | 90-114 | 105-129 | 120-144 | 135-159 | 150-170 |
|---|---|---|---|---|---|---|---|---|---|---|---|---|
| MS 10 | + | - | - | - | - | - | - | + | - | - | + | - |
| MS 17 | + | - | - | - | - | - | + | - | - | - | - | + |
| MS 41 | + | - | - | + | - | - | - | + | - | - | + | - |
| MS 49 | + | - | + | - | - | - | - | - | - | - | - | + |
| MS 57 | + | - | - | + | - | - | + | - | - | - | - | - |
| MS 59 | + | - | - | - | - | - | - | - | - | - | - | - |
| MS 60 | + | - | - | - | - | - | + | - | - | - | - | - |
| MS 43 | + | - | - | - | - | - | - | - | - | - | - | - |

Response to MBP peptides in MS patients: 3rd time point

| | MBP | 1 to 24 | 15-39 | 30-54 | 45-69 | 60-84 | 75-99 | 90-114 | 105-129 | 120-144 | 135-159 | 150-170 |
|---|---|---|---|---|---|---|---|---|---|---|---|---|
| MS 41 | + | - | - | - | - | - | + | - | - | - | - | - |
| MS 60 | + | - | - | + | - | - | - | - | - | + | + | - |
| MS 59 | + | - | - | - | - | - | - | - | - | - | + | - |

FIG. 2

| TCC | MBP region | Specific peptide |
|---|---|---|
| MS 39 : A7* | 1-24 | 5-19 |
| MS 49 : D3* | 30-54 | 30-44 |
| MS 49 : C8* | 30-54 | 30-44 |
| MS 49 : A8* | 30-54 | 30-44 |
| MS 48 : B6* | 30-54 | 30-44 |
| MS 39 : D7* | 60-84 | 60-74 |
| MS 43 : A7* | 75-99 | 83-99 |
| MS 41 : B6* | 75-99 | 83-99 |
| MS 41 : A2* | 75-99 | 83-99 |
| MS 41 : C6* | 75-99 | 83-99 |
| N5 : 8** | 75-99 | 83-99 |
| MS 60 : A2* | 105-129 | 110-124 |
| MS 60 : B3* | 105-129 | 110-124 |
| MS 60 : E1* | 120-144 | 130-144 |
| MS 17 : A3* | 120-144 | 130-144 |
| MS 60 : F7* | 135-159 | 140-154 |
| MS 60 : D1* | 135-159 | 140-154 |
| MS 57 : A1* | 135-159 | 140-154 |
| MS 59 : F1* | 135-159 | 140-154 |
| N5 : 19** | 135-159 | 140-154 |
| MS 43 : A3* | 150-170 | 156-169 |
| MS 43 : D2* | 150-170 | 156-169 |

FIG. 6

| PROTEIN REGION STUDIED | EPITOPES IDENTIFIED USING T CELL CLONES |
|---|---|
| 1-24 | 5-19 |
| 15-39 | Not common |
| 30-54 | 30-44 |
| 45-69 | Not common |
| 60-84 | 60-74 |
| 75-99 | 80-94<br>83-99 |
| 90-114 | Not common |
| 105-29 | 110-124 |
| 120-144 | 130-144 |
| 135-159 | 130-144<br>140-154 |
| 150-170 | 150-164<br>156-169 |

FIG. 7A

| EPITOPE STUDIED | APITOPE STUDIED |
|---|---|
| 5-19 | Not done |
| 30-44 | ++ |
| 60-74 | Not done |
| 80-94 | ++ |
| 83-99 | ++ |
| 110-124 | ++ |
| 130-144 | ++ |
| 140-154 | Not done |
| 156-170 | - |

FIG. 7B

| Time point | MBP | 1-24 | 15-39 | 30-54 | 45-69 | 60-84 | 75-99 | 90-114 | 105-129 | 120-144 | 135-159 | 150-170 |
|---|---|---|---|---|---|---|---|---|---|---|---|---|
| MS 10    1 | 14 | 17 | 3 | 15 | 55 | 1 | 1 | 2 | 15 | 1 | 2 | 1 |
| 2 | 4 | 1 | <1 | <1 | <1 | <1 | 9 | 4 | 1 | <1 | 4 | 1 |
| 3 | 8 | 3 | 1 | 1 | 1 | <1 | 1 | 1 | 2 | 1 | 1 | 0 |
| MS 17    1 | 29 | 1 | 1 | 1 | 1.5 | 2 | 1 | <1 | <1 | 1 | 1.5 | 2 |
| 2 | 51 | 1 | <1 | 1 | <1 | <1 | 1 | <1 | <1 | <1 | 1 | 5 |
| 3 | 51 | 1 | 1 | 1 | 1 | 1 | <1 | 2 | 2 | 1 | 1 | 1 |
| MS 19    1 | 1 | 2 | 1 | <1 | <1 | <1 | <1 | <1 | <1 | <1 | <1 | <1 |
| 2 | 1.5 | <1 | <1 | 1 | 1 | <1 | <1 | <1 | <1 | <1 | <1 | <1 |
| MS 39    1 | 39 | 3 | 5 | 1 | 3 | 2 | 2 | 7.5 | 6 | <1 | 2 | 2 |
| 2 | 58 | 1 | <1 | <1 | 2 | 2 | <1 | <1 | <1 | <1 | <1 | <1 |
| 3 | 50 | 8 | 1 | <1 | 1 | 2 | 1 | 1.5 | 1 | <1 | 3 | 1 |
| MS 41    1 | 59 | 2 | 3 | 2 | 2 | 1.5 | 1 | 1 | 2 | 6 | 7 | 3 |
| 2 | 116 | <1 | 1 | <1 | <1 | <1 | <1 | <1 | 1 | <1 | <1 | <1 |
| 3 | 74 | 2 | 1.5 | 1 | 2 | 2 | 8 | 1.5 | <1 | <1 | 95 | <1 |
| MS 43    1 | 32 | 4 | 22 | 3 | 3 | 3 | 24 | 4 | 2 | 12 | 3 | 4 |
| 2 | 75 | <1 | <1 | <1 | 2 | 3 | <1 | <1 | 2 | <1 | <1 | <1 |
| 3 | 66 | 2 | 2 | 1 | 13 | 2 | 1 | 2 | 2 | 1 | 7 | 1 |
| MS 49    1 | 6 | 5 | 9 | 11 | 5 | 4 | 11 | 4 | 35 | 6 | 5 | 31 |
| 2 | 202 | 2 | 8 | 23 | 4 | 3 | 2 | 73 | 2 | 2 | 11 | 34 |
| 3 | 2 | 1 | 2 | 4 | 1 | 2 | 1 | 2 | 1 | 1 | 1 | 2 |
| MS 57    1 | 36 | 8 | <1 | 1.5 | 1 | 1 | 2 | 2 | <1 | <1 | <1 | <1 |
| 2 | 7 | 2 | 2 | 2 | 2 | 1 | 1 | <1 | 1 | 1 | <1 | <1 |
| 3 | 6 | <1 | <1 | <1 | 1 | 1 | 1 | 1 | 2 | 1 | 1 | 2 |
| MS 59    1 | 57 | 2 | 1 | 1 | 1 | 1 | 2 | 2 | 1 | 1 | 2 | 14 |
| 2 | 27 | 1 | 9 | 2 | 2 | 1 | 9 | <1 | 2 | 1 | 1 | 1 |
| 3 | 14 | 1 | <1 | 2 | <1 | 1 | 4 | <1 | <1 | 63 | 137 | 1 |
| MS 60    1 | 44 | 3 | 2 | 19 | 8 | 2 | 28 | 9 | 11 | 16 | 16 | 12 |
| 2 | 133 | 1 | <1 | 83 | <1 | <1 | 20 | <1 | 1 | 2 | 2 | <1 |
| 3 | 23 | 2 | <1 | 13 | <1 | 2 | <1 | <1 | <1 | 10 | 26 | 2 |
| MS 67    1 | 49 | 2 | 3 | 2 | 1 | 2 | 2 | 1 | <1 | 1 | 1 | 58 |

FIG. 10

| MBP | 1-24 | 15-39 | 30-54 | 45-69 | 60-84 | 75-99 | 90-114 | 105-129 | 120-144 | 135-159 | 150-170 |
|---|---|---|---|---|---|---|---|---|---|---|---|
| N1 | 20 | <1 | <1 | <1 | <1 | 0 | 1 | <1 | 1 | <1 | <1 | <1 |
| N2 | 54 | <1 | <1 | <1 | <1 | <1 | <1 | <1 | <1 | <1 | <1 | <1 |
| N3 | 14 | 2 | 2 | 2 | 1 | 4 | 6 | 1 | 1 | <1 | 2 | 3 |
| N4 | 6 | 1 | 1.5 | <1 | <1 | <1 | 1 | 1 | <1 | <1 | 1 | <1 |
| N5 | 27 | <1 | 1.5 | <1 | <1 | <1 | 1.5 | 1 | <1 | <1 | 1 | <1 |
| N6 | 29 | 5 | 1 | 1 | 3 | 2 | 5 | 6 | 2 | 2 | 3 | 2 |
| N7 | 100 | 2 | <1 | 2 | <1 | <1 | <1 | 1 | 1 | <1 | 2 | 2 |
| N8 | 33 | 3 | <1 | 1.5 | <1 | 1 | 1 | <1 | 1 | 1 | 2.5 | 1.5 |
| N9 | 104 | <1 | <1 | 2 | <1 | 2 | 1.5 | <1 | <1 | 2 | 1 | <1 |
| N10 | 72 | 3 | <1 | 1 | <1 | 12 | 5 | <1 | 2 | 71 | 5 | <1 |
| N11 | 11 | 4 | 1 | 18 | <1 | <1 | 1 | <1 | <1 | 7 | 7 | 8 |
| N12 | 89 | 1 | <1 | <1 | <1 | <1 | 1 | 1 | <1 | <1 | <1 | <1 |

PEPTIDE COMPOSITION

CROSS-REFERENCE TO RELATED APPLICATIONS

This Patent application is a Continuation-in-part of U.S. patent application Ser. No. 10/362,264, filed Jun. 5, 2003 (pending), which is a Continuation under 35 U.S.C. 111(a) of International Patent Application No. PCT/GB01/03702, filed Aug. 17, 2001 and published in English as International Patent Application No. WO 02/16410 A2 on Feb. 28, 2002, which claims priority from Patent Application No. GB 0114547.3, filed on Jun. 14, 2001, and Patent Application No. GB 0020618.5, filed Aug. 21, 2000.

FIELD OF THE INVENTION

The present invention relates to a method for selecting a tolerogenic peptide, a peptide identified by such a method and its use in the treatment and/or prevention of a disease. The present invention also relates to a pharmaceutical composition comprising a plurality of such tolerogenic peptides, such as a composition which comprises myelin basic protein (MBP) peptides. The composition may be used for the treatment of multiple sclerosis.

BACKGROUND OF THE INVENTION

In an adaptive immune response, T lymphocytes are capable of recognising internal epitopes of a protein antigen. Antigen presenting cells (APC) take up protein antigens and degrade them into short peptide fragments. A peptide may bind to a major histocompatability complex (MHC) class I or II molecule inside the cell and be carried to the cell surface. When presented at the cell surface in conjunction with an MHC molecule, the peptide may be recognised by a T cell (via the T cell receptor (TCR)), in which case the peptide is a T cell epitope.

T cell epitopes play a central role in the adaptive immune response to any antigen, whether self or foreign. The central role played by T cell epitopes in hypersensitivity diseases (which include allergy, autoimmune diseases and transplant rejection) has been demonstrated through the use of experimental models. It is possible to induce inflammatory or allergic diseases by injection of synthetic peptides (based on the structure of T cell epitopes) in combination with adjuvant.

By contrast, it has been shown to be possible to induce immunological tolerance towards particular peptide epitopes by administration of peptide epitopes in soluble form. Administration of soluble peptide antigens has been demonstrated as an effective means of inhibiting disease in experimental autoimmune encephalomyelitis (EAE—a model for multiple sclerosis (MS)) (Metzler and Wraith (1993) Int. Immunol. 5:1159-1165; Liu and Wraith (1995) Int. Immunol. 7:1255-1263; Anderton and Wraith (1998) Eur. J. Immunol. 28:1251-1261); and experimental models of arthritis, diabetes, and uveoretinitis (reviewed in Anderton and Wraith (1998) as above). This has also been demonstrated as a means of treating an ongoing disease in EAE (Anderton and Wraith (1998) as above).

The use of tolerogenic peptides to treat or prevent disease has attracted considerable attention. One reason for this is that it has been shown that certain tolerogenic epitopes can down-regulate responses of T cells for distinct antigens within the same tissue. This phenomenon, known as "bystander suppression" means that it should be possible to induce tolerance to more than one epitope (preferably all epitopes) within a given antigen, and to more than one antigen for a given disease, using a particular tolerogenic peptide (Anderton and Wraith (1998) as above). This would obviate the need to identify all of the pathogenic antigens within a particular disease.

Peptides are also a favourable option for therapy because of their relatively low cost and the fact that peptide analogues can be produced with altered immunological properties. Peptides may thus be modified to alter their interactions with either MHC or TCR.

One possible problem with this approach is that it has been shown that not all peptides which act as T cell epitopes are capable of inducing tolerance. The myelin basic protein (MBP) peptide 89-101 is an immunodominant antigen after immunisation and is also a very effective immunogen both in terms of priming for T cell reactivity and induction of EAE. However, this peptide has been shown to be ineffective at inducing tolerance when administered in solution (Anderton and Wraith (1998), as above).

A number of explanations for the observed hierarchy in the ability of T cell epitopes to induce tolerance have been proposed (reviewed in Anderton and Wraith (1998) as above). In particular, it has been proposed that there is a correlation between the affinity of the peptide for the MHC and tolerogenicity (Liu and Wraith (1995) as above), but this does not tally with some of the observations. For example, MBP[89-101], which is not tolerogenic, binds to I-A$^S$ with relatively high affinity. It is thus not straightforward to predict which peptides will induce tolerance.

If there were a rational explanation why only a proportion of peptide epitopes are capable of inducing tolerance, this would facilitate the selection of tolerogenic peptides useful in treating and preventing hypersensitivity disorders.

Multiple Sclerosis

Multiple Sclerosis (MS) is the most common disabling neurological condition affecting young adults. Around 85,000 people in the UK have MS.

In multiple sclerosis (MS), inflammation of nervous tissue causes loss of myelin, a fatty material that acts as a protective insulation for nerve fibres in the brain and the spinal cord. This loss of myelin, or demyelination, leaves multiple areas of scar tissue, or sclerosis, along nerve cells. Consequently, the sclerosis results in multiple and varied neurological signs and symptoms, usually with repeated relapse and remission.

Common symptoms of MS include reduced or loss of vision, stumbling and uneven gait, slurred speech, as well as urinary frequency and incontinence. In addition, MS can cause mood changes and depression, muscle spasms and severe paralysis.

It is now generally accepted that MS is an autoimmune disease mediated by autoreactive T-cells.

Current treatments for MS generally suppress the immune system. For example, one treatment includes transplantation of bone marrow along with administration of cytostatics and immunosuppressive drugs. This treatment is effective for some patients, but it is expensive and relatively high-risk. Additionally, the administration of cytostatics is considered controversial in treating MS because its effects are unclear and potential side-effects are severe.

Treatment with interferon-beta (IFNβ) reduces the symptoms of MS in some patients and is therefore widely used. However, the mechanism of action of interferon-beta is unclear and IFNβ treatment is ineffective for many patients.

Currently, an effective treatment for MS does not exist. Treatment is focused on merely reducing its symptoms, usually by general suppression of the immune system.

Synthetic Peptides

Metzler and Wraith (Int. Immunol. 5:1159-1165 (1993)) were the first researchers to describe the use of synthetic peptides to induce suppression of an autoimmune response in the mouse experimental autoimmune encephalomyelitis (EAE) model, a commonly used in vivo model of MS. In this study, peptides derived from MBP were administered by the intranasal route, and it was found that the level of disease suppression correlated with the antigenic strength of the peptide used.

Later, in 1995, Liu and Wraith (Int. Immunol. 7:1255-1263) showed that it was also possible to induce suppression of EAE in mice by the intraperitoneal administration of soluble MBP-derived peptides. In this study, suppression of both Th1 and Th2 responses was achieved, and it was shown that administration of peptides after the start of an immune response could lead to suppression of the on-going immune reaction.

However, it was found that not all peptides capable of acting as T-cell epitopes are capable of inducing tolerance. The myelin basic protein (MBP) peptide 89-101 is an immunodominant antigen after immunisation and is also a very effective immunogen both in terms of priming for T cell reactivity and induction of EAE. However, this peptide has been shown to be ineffective at inducing tolerance when administered in solution (Anderton and Wraith (1998) Eur. J. Immunol. 28:1251-1261).

The present inventors have previously shown that there is a link between the capacity of a peptide to bind to an MHC class I or II molecule and be presented to a T cell without further antigen processing and its capacity to induce tolerance in vivo. Peptides which are antigen processing independent (i.e. do not require further antigen processing to bind MHC) can be predicted to be tolerogenic in vivo. These peptides have been termed "APITOPEs", for Antigen Processing Independent epiTOPES. APITOPE is a trademark of Apitope Technology (Bristol) Ltd.

WO 03/064464 identifies the following additional MBP peptides as being APITOPEs: 134-148; 135-149; 136-150; 137-151; 138-152 and 140-154.

BRIEF SUMMARY OF THE INVENTION

The present inventors have shown that if a peptide epitope is of an appropriate size to be presented by immature APC without antigen processing, it can induce immunological tolerance. The observation that some T cell epitopes are tolerogenic and others are incapable of inducing tolerance can therefore be explained by the fact that some epitopes require further processing before they are capable of being presented by an MHC molecule. These epitopes which require further processing do not induce tolerance when administered in a soluble form, despite their capacity to induce disease when injected in combination with adjuvant.

The epitopes which do not require further processing are capable of inducing tolerance, and have been termed "APITOPEs" (Antigen Processing Independent epiTOPES) by the inventors.

This finding provides a rule-based method for selection of tolerogenic T cell epitopes which obviates the need to examine the tolerogenic capacity of a peptide in vivo. This is particularly advantageous in the development of strategies to treat or prevent diseases for which no animal models are available. Even for diseases which have an animal model, the selection method should make the development of tolerance-inducing compositions simpler and safer, because it provides a mechanism whereby the tolerance induction capacity of a peptide can be tested on human T cells (recognising antigen in conjunction with human MHC molecules) in vitro, prior to their use in vivo.

In a first aspect, therefore, the present invention provides a method for selecting a tolerogenic peptide which comprises the step of selecting a peptide which is capable of binding to an MHC class I or class II molecule without further processing.

In a preferred embodiment, the peptide is capable of binding to an MHC class II molecule without further processing.

A number of methods are known in the art for screening for peptides which are capable of acting as T cell epitopes for a given antigen. Commonly, therefore, the method will be used to select a tolerogenic peptide from a plurality of peptides each comprising a T cell epitope.

In order to investigate whether a peptide is capable of binding to an MHC class I or II molecule without further processing, one can study the capacity of the peptide to bind MHC class I or II molecules using an antigen processing independent presentation system (APIPS). In a preferred embodiment, therefore the method comprises the following steps:
  (i) treating an APIPS with a peptide; and
  (ii) analyzing binding of the peptide to MHC class I or II molecules within the APIPS.

In a second aspect, the present invention provides peptide selected by the method of the first aspect of the invention.

The peptide may be useful in the treatment and/or prevention of a disease. In particular, the peptide may be useful in the treatment and/or prevention of a disease which is mediated by autoreactive T cells. Hypersensitivity reactions are particularly amenable to treatment/prevention using the peptide of the present invention, for example allergy, autoimmunity and transplant rejection.

The present inventors have already identified a number of APITOPEs for myelin basic protein, which is an autoantigen in multiple sclerosis. In an especially preferred embodiment, therefore, the peptides of the present invention are useful in the treatment and/or prevention of multiple sclerosis.

It is known that some peptides are capable of inducing tolerance to other epitopes from the same antigen, and even other epitopes from a distinct antigen (by the phenomenon known as bystander suppression). However, the present inventors predict that in order to adequately suppress all the autoreactive T cells, it would be advantageous for a combination of various APITOPEs to be administered to the patient to treat/prevent a particular disease. In a third aspect, therefore, the present invention provides a pharmaceutical composition comprising a plurality of peptides according to the second aspect of the invention, each peptide being based on a T cell epitope.

In a fourth aspect, the present invention provides a method for treating and/or preventing a disease in a subject which comprises the step of administering a peptide according to the second aspect of the invention to the subject.

A general strategy for treating and/or preventing a disease in a subject may comprise the following steps:
  (i) identifying an antigen for the disease
  (ii) identifying an APITOPE for the antigen; and
  (iii) administering the APITOPE to the subject.

The present inventors have now found that a "cocktail" of four MBP peptides, all of which are APITOPEs, is particularly effective in treating MS. It is thought that the four peptides exert a synergistic effect when in combination.

In a fifth aspect, therefore, the present invention relates to a composition which comprises the following myelin basic protein peptides:

MBP 30-44;
MBP 83-99;
MBP 131-145; and
MBP 140-154.

The composition may consist essentially of MBP 30-44, 83-99, 131-145 and 140-154.

The composition may be used for treating or preventing a disease, in particular multiple sclerosis.

The composition may be used for treating or preventing optic neuritis, in particular optic neuritis associated with multiple sclerosis.

In a sixth aspect, the present invention relates to a method of treating or preventing multiple sclerosis and/or optic neuritis by administering a composition according to the first aspect of the invention to a subject.

In the method of the sixth aspect of the invention the composition may be administered following a dose-escalation protocol.

It has been found that two of the peptides in the cocktail are HLA-DQ6 binding (MBP 30-44 and 131-145) and two are HLA-DR2 binding (MBP 140-154 and 83-99). The combined use of these APITOPEs provides more widespread cover of the different Major Histocompatibility Complex (MHC) haplotypes seen in MS patients than therapy with a single peptide.

The method of the sixth aspect of the invention may involve administration of the composition to a HLA-DQ6 or HLA-DR2 positive subject.

In a seventh aspect, the present invention provides a kit which comprises the following myelin basic protein peptides:
MBP 30-44;
MBP 83-99;
MBP 131-145; and
MBP 140-154
for simultaneous, separate or sequential administration.

BRIEF DESCRIPTION OF THE FIGURES

FIG. 2 is a table which summarises PBMC responses to MBP and its peptides in MS patients. Certain individuals are analysed on three separate time points, with a period of approximately 4 to 7 months between each time point.

FIG. 6 shows a map of the fine specificity of the peptide regions identified in the kinetic response assay which is obtained through the use of TCC generated from MS patients and healthy individuals. Most of the peptides used in screening assays are 15-mer in length, however a few are 10-mer, and 1 peptide is 17-mer. The specificity of each TCC is tested at least twice.

FIG. 7A is a table showing the characterization of T cell epitopes within myelin basic protein recognised by T lymphocytes from MS patients.

FIG. 7B is a table showing that all T cell epitopes are not necessarily presented by fixed APC and therefore not APITOPEs.

FIG. 10 is a table which shows peak Stimulation Index (SI) values to MBP and MBP-peptides in MS patients obtained on three separate time points. Samples for the second time point were collected 4-8 months following the $1^{st}$ time point, and samples for the $3^{rd}$ time point were obtained 3-5 months following the second time point. Background cpm was measured for each day and varied between 80-700 cpm; a positive response (bold) was defined according to SI>3 and δcpm>1000. (It was not possible to collect samples for all three time points from patients MS 19 and MS 67).

FIG. 11 is a table which shows peak Stimulation Index (SD values to MBP and MBP-peptides in healthy individuals. Background cpm was measured for each day and varied between 80-700 cpm; a positive response (bold) was defined according to SI>3 and dcpm>1000.

FIG. 23 shows an example of Snellens chart.

DETAILED DESCRIPTION OF THE INVENTION

Figure 1A:
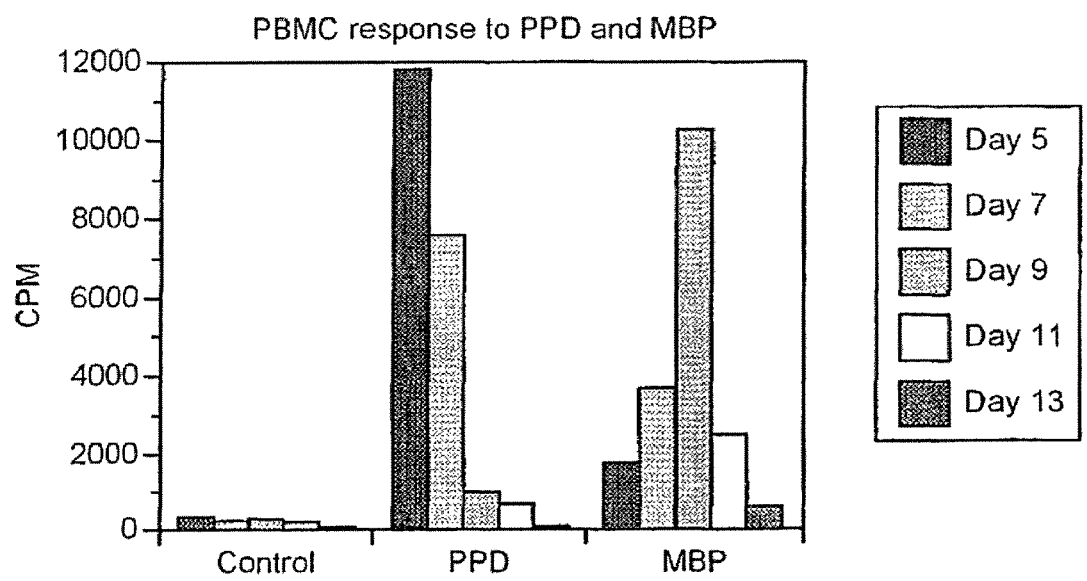
FIG. 1 shows a typical example of the kinetic profile to *Mycobacterium tuberculosis* purified protein derivative (PPD) and MBP in Multiple Sclerosis (MS) patients and healthy individuals. Peripheral blood mononuclear cells (PBMC) isolated from an MS patient (A) and normal individual (B) are tested for their ability to proliferate in the presence of PPD and whole MBP; the kinetic profile of the proliferative response to MBP is compared with that of secondary antigen PPD.

In a first aspect, the present invention relates to a method for selecting a tolerogenic peptide.

Tolerance

As used herein, the term "tolerogenic" means capable of inducing tolerance.

Tolerance is the failure to respond to an antigen. Tolerance to self antigens is an essential feature of the immune system, when this is lost, autoimmune disease can result. The adaptive immune system must maintain the capacity to respond to an enormous variety of infectious agents while avoiding autoimmune attack of the self antigens contained within its own tissues. This is controlled to a large extent by the sensitivity of immature T lymphocytes to apoptotic cell death in the thymus (central tolerance). However, not all self antigens are detected in the thymus, so death of self-reactive thymocytes remains incomplete. There are thus also mechanisms by which tolerance may be acquired by mature self-reactive T lymphocytes in the peripheral tissues (peripheral tolerance). A review of the mechanisms of central and peripheral tolerance is given in Anderton et al (1999) (*Immunological Reviews* 169:123-137).

Tolerance may result from or be characterised by the induction of anergy in at least a portion of CD4+ T cells. In order to activate a T cell, a peptide must associate with a "professional" APC capable of delivering two signals to T cells. The first signal (signal 1) is delivered by the MHC-peptide complex on the cell surface of the APC and is received by the T cell via the TCR. The second signal (signal 2) is delivered by costimulatory molecules on the surface of the APC, such as CD80 and CD86, and received by CD28 on the surface of the T cell. It is thought that when a T cell receives signal 1 in the absence of signal 2, it is not activated and, in fact, becomes anergic. Anergic T cells are refractory to subsequent antigenic challenge, and may be capable of suppressing other immune responses. Anergic T cells are thought to be involved in mediating T cell tolerance.

Without wishing to be bound by theory, the present inventors predict that peptides which require processing before they can be presented in conjunction with MHC molecules do not induce tolerance because they have to be handled by mature antigen presenting cells. Mature antigen presenting cells (such as macrophages, B cells and dendritic cells) are capable of antigen processing, but also of delivering both signals 1 and 2 to a T cell, leading to T cell activation. APITOPEs, on the other hand, will be able to bind class II MHC on immature APC. Thus they will be presented to T cells without costimulation, leading to T cell anergy and tolerance.

Of course, APITOPEs are also capable of binding to MHC molecules at the cell surface of mature APC. However, the immune system contains a greater abundance of immature than mature APC (it has been suggested that less than 10% of dendritic cells are activated, Summers et al. (2001) Am. J. Pathol. 159: 285-295). The default position to an APITOPE will therefore be anergy/tolerance, rather than activation.

It has been shown that, when tolerance is induced by peptide inhalation, the capacity of antigen-specific CD4+ T cells to proliferate is reduced. Also, the production of IL-2, IFN-γ and IL-4 production by these cells is down-regulated, but production of IL-10 is increased. Neutralisation of IL-10 in mice in a state of peptide-induced tolerance has been shown to restore completely susceptibility to disease. It has been proposed that a population of regulatory cells persist in the tolerant state which produce IL-10 and mediate immune regulation (Burkhart et al (1999) Int. Immunol. 11:1625-1634).

The induction of tolerance can therefore be monitored by various techniques including:
(a) reduced susceptibility to contract the disease for which the peptide is a target epitope in vivo;
(b) the induction of anergy in CD4+ T cells (which can be detected by subsequent challenge with antigen in vitro);
(c) changes in the CD4+ T cell population, including
   (i) reduction in proliferation;
   (ii) down-regulation in the production of IL-2, IFN-γ and IL-4; and
   (iii) increase in the production of IL-10.

Antigen Processing Independent Epitopes (APITOPEs)

The method of the present invention comprises the step of selecting a peptide which is capable of binding to an MHC class I or II protein without further processing. Such peptides are known herein as "APITOPEs" (Antigen Processing Independent epiTOPES).

Cell surface presentation of peptides derived from a given antigen is not random and tends to be dominated by a small number of frequently occurring epitopes. The dominance of a particular peptide will depend on many factors, such as relative affinity for binding the MHC molecule, spatio-temporal point of generation within the APC and resistance to degradation. The epitope hierarchy for an antigen can change with progression of an immune response, which has important implications for self-tolerance and autoimmunity. Immunodominant determinant regions are likely to be good tolerogens. Hence, in a preferred embodiment, the APITOPE of the present invention is based on a dominant epitope.

However, after a primary immune response to the immunodominant peptides, epitope "spreading" may occur to subdominant determinants (Lehmann et al (1992) Nature 358: 155-157). Presentation of sub-dominant epitopes may be important in triggering autoimmunity. The APITOPE of the present invention may, therefore be based on a subdominant epitope.

For any given antigen, cryptic epitopes may also exist. Cryptic epitopes are those which can stimulate a T cell response when administered as a peptide but which fail to produce such a response when administered as a whole antigen. It may be that during processing of the antigen into peptides in the APC the cryptic epitope is destroyed. The present inventors have shown that peptide 92-98 is a cryptic epitope for MBP (Example 2C). Interestingly there is a putative cleavage site for asparaginyl endopeptidase within this peptide region, which may mean that during natural processing, no peptides containing this region are generated by the APC.

A cryptic epitope may act as an APITOPE in vitro, in that it may be capable of binding to an MHC molecule without further processing, and inducing anergy in a T cell which recognises the cryptic epitope. However, such an APITOPE would be unlikely to be therapeutically useful because it should be incapable of tolerizing T cells which recognise a naturally processed epitope of the antigen.

Epitopes for an antigen may be identified by measuring the T cell response to overlapping peptides spanning the entire antigen (see below) when presented by APC. Such studies usually result in "nested sets" of peptides, and the minimal epitope for a particular T cell line/clone can be assessed by measuring the response to truncated peptides.

It cannot be assumed that a minimal epitope of an antigen will behave as an APITOPE. It may well be that amino acids flanking the minimal epitope will be required for optimal binding to the MHC. The APITOPE should be designed to cover the possibility that there may be subtle differences between the minimal epitopes of different T cell clones.

It should be emphasised that it may not be possible to identify an APITOPE for all epitopes. There is clear evidence that some epitopes bind MHC in a way that is dependent on MHC-loading in endosomes and hence require processing (Viner et al (1995) Proc. Natl. Acad. Sci. 92:2214-2218). This is another reason why one cannot assume that each minimal epitope will inevitably behave as an APITOPE.

Identification of Peptides Containing T Cell Epitopes

There are a number of methods known in the art to identify the T cell epitopes within a given antigen.

Naturally processed epitopes may be identified by mass spectrophotometric analysis of peptides eluted from antigen-loaded APC. These are APC that have either been encouraged to take up antigen, or have been forced to produce the protein intracellularly by transformation with the appropriate gene. Typically APC are incubated with protein either in solution or suitably targeted to the APC cell surface. After incubation at 37° C. the cells are lysed in detergent and the class II protein purified by, for example affinity chromatography. Treatment of the purified MHC with a suitable chemical medium (for example, acid conditions) results in the elution of peptides from the MHC. This pool of peptides is separated and the profile compared with peptide from control APC treated in the same way. The peaks unique to the protein expressing/fed cells are analysed (for example by mass spectrometry) and the peptide fragments identified. This procedure usually generates information about the range of peptides (usually found in "nested sets") generated from a particular antigen by antigen processing.

Another method for identifying epitopes is to screen a synthetic library of peptides which overlap and span the length of the antigen in an in vitro assay. For example, peptides which are 15 amino acids in length and which overlap by 5 or 10 amino acids may be used. The peptides are tested in an antigen presentation system which comprises antigen presenting cells and T cells. For example, the antigen presentation system may be a murine splenocyte preparation, a preparation of human cells from tonsil or PBMC. Alternatively, the antigen presentation system may comprise a particular T cell line/clone and/or a particular antigen presenting cell type.

T cell activation may be measured via T cell proliferation (for example using $^3$H-thymidine incorporation) or cytokine production. Activation of TH1-type CD4+ T cells can, for example be detected via IFNγ production which may be detected by standard techniques, such as an ELISPOT assay.

Overlapping peptide studies usually indicate the area of the antigen in which an epitope is located. The minimal epitope for a particular T cell can then be assessed by measuring the response to truncated peptides. For example if a response is obtained to the peptide comprising residues 1-15 in the overlapping library, sets which are truncated at both ends (i.e. 1-14, 1-13, 1-12 etc. and 2-15, 3-15, 4-15 etc.) can be used to identify the minimal epitope.

The identification of immunodominant regions of an antigen using in vitro assays (especially those using T cell lines) is predicted to present a skewed pattern of peptide reactivity by the present inventors. In the study to identify MBP epitopes which is described in the examples, they use a kinetic response assay in which the proliferation of PBMC from MS patients and healthy individuals is measured against an overlapping peptide library. This assay is based on the finding that, although T cells form normal individuals and MS patients respond in a similar fashion to purified protein antigen, they respond in a different way to peptides based on the sequence of MBP. T cells from MS patients respond with greater magnitude and more rapid kinetics to peptide antigens when compared with normal healthy donors. This enables screening for and identification of the epitope to which the particular patient responds at a particular time. In the study described herein, this approach has revealed a number of epitope-containing regions that were not identified using standard techniques. Moreover is it shown that T cell recognition exhibits a cyclical pattern, appearing at one time point, regressing, and subsequently reappearing at a later date.

The kinetic assay described by the inventors provides a valuable tool because it reveals the epitope to which a patient is responding at a particular time. This information may be used to tailor a therapeutic APITOPE-administration approach for a particular patient by identifying and administering an APITOPE for the relevant epitope (if there is one). This information may also enable a general pattern to be drawn up for disease progression, so that the therapeutic composition can be designed to include APITOPEs to the epitopes which are likely to be present at a given stage during the disease.

Antigen Processing Independent Presentation Systems (APIPS)

Once an epitope has been identified, the next step is to investigate whether it also behaves as an APITOPE.

An APITOPE must be presented to T cells without the need for antigen processing. Having identified peptides containing T cell epitopes, APITOPEs may be identified using a processing free system. Truncated peptides and peptide analogues may be tested for activation using an antigen processing independent presentation system (APIPS).

Examples of APIPS Include:
a) fixed APC (with or without antibodies to CD28);
b) Lipid membranes containing Class I or II MHC molecules (with or without antibodies to CD28); and
c) purified natural or recombinant MHC in plate-bound form (with or without antibodies to CD28).

It is known to use fixed APC to investigate T cell responses, for example in studies to investigate the minimal epitope within a polypeptide, by measuring the response to truncated peptides (Fairchild et al (1996) Int. Immunol. 8:1035-1043). APC may be fixed using, for example formaldehyde (usually paraformaldehyde) or glutaraldehyde.

Lipid membranes (which may be planar membranes or liposomes) may be prepared using artificial lipids or may be plasma membrane/microsomal fractions from APC.

In use, the APIPS may be applied to the wells of a tissue culture plate. Peptide antigens are then added and binding of the peptide to the MHC portion of the APIPS is detected by addition of selected T cell lines or clones. Activation of the T cell line or clone may be measured by any of the methods known in the art, for example via $^3$H-thymidine incorporation or cytokine secretion.

Peptides

The second aspect of the invention relates to a peptide.

The term "peptide" is used in the normal sense to mean a series of residues, typically L-amino acids, connected one to the other typically by peptide bonds between the α-amino and carboxyl groups of adjacent amino acids The term includes modified peptides and synthetic peptide analogues.

A peptide of the present invention may be any length that is capable of binding to an MHC class I or II molecule without further processing.

Peptides that bind to MHC class I molecules are typically 7 to 13, more usually 8 to 10 amino acids in length. The binding of the peptide is stabilised at its two ends by contacts between atoms in the main chain of the peptide and invariant sites in the peptide-binding groove of all MHC class I molecules. There are invariant sites at both ends of the groove which bind the amino and carboxy termini of the peptide. Variations is peptide length are accommodated by a kinking in the peptide backbone, often at proline or glycine residues that allow the required flexibility.

Peptides which bind to MHC class II molecules are typically between 8 and 20 amino acids in length, more usually between 10 and 17 amino acids in length, and can be much longer. These peptides lie in an extended conformation along the MHC II peptide-binding groove which (unlike the MHC class I peptide-binding groove) is open at both ends. The peptide is held in place mainly by main-chain atom contacts with conserved residues that line the peptide-binding groove.

The peptide of the present invention may be made using chemical methods (Peptide Chemistry, A practical Textbook. Mikos Bodansky, Springer-Verlag, Berlin.). For example, peptides can be synthesized by solid phase techniques (Roberge JY et al (1995) Science 269: 202-204), cleaved from the resin, and purified by preparative high performance liquid chromatography (e.g., Creighton (1983) Proteins Structures And Molecular Principles, WH Freeman and Co, New York N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage from a longer polypeptide. For example, the peptide may be obtained by cleavage from the target antigen. The composition of a peptide may be confirmed by amino acid analysis or sequencing (e.g., the Edman degradation procedure).

In a preferred embodiment the peptide is derivable from a target antigen. A target antigen is a molecule (for example a protein or glycoprotein) which is processed by APC and recognised by T cells during the course of the disease. The target antigen will, of course, depend on the target disease. Preferably the peptide is derivable from a fragment of the antigen which arises by natural processing of the antigen by an APC.

For practical purposes, there are various other characteristics which the peptide should show. For example, the peptide should be soluble at a concentration which permits its use in vivo. Preferably the peptide should be soluble at concentrations of up to 0.5 mg/ml, more preferably the peptide should be soluble at concentrations of up to 1 mg/ml, most preferably the peptide should be soluble at concentrations of up to 5 mg/ml.

For intranasal administration the maximum volume of dose which can be taken up using current procedures is approximately 200 μl per nostril. If the peptide is soluble at 1 mg/ml, a double dose to each nostril enables 800 μg to be given to the patient. It is unusual to give more that 5 mg in any individual dose.

It is also important that the peptide is sufficiently stable in vivo to be therapeutically useful. The present inventors have found that in vivo, 30 minutes after administration the total amount of a test peptide drops to about 50%, 4 hours after administration the amount drops to about 30%, but that after 5 days the peptide is still detectable (at about 5%). The half-life of the peptide in vivo should be at least 10 minutes, preferably at least 30 minutes, more preferably at least 4 hours, most preferably at least 24 hours.

The present inventors have found that following intranasal administration, the amount of peptide in the draining lymph node peaks at about 4 hrs following administration, however peptide is still detectable (at levels of about 5% maximum) after 5 days. Preferably the peptide is sufficiently stable to be present at a therapeutically active concentration in the draining lymph node for long enough to exert a therapeutic effect.

The peptide should also demonstrate good bioavailability in vivo. The peptide should maintain a conformation in vivo which enables it to bind to an MHC molecule at the cell surface without due hindrance.

Target Diseases

In one embodiment, the peptide of the second aspect of the invention is for use in the treatment and/or prevention of a disease.

An APITOPE for MHC class II is likely to be particularly useful in diseases which are mediated by CD4+ T cell responses. For example, diseases which are established or maintained by an inappropriate or excessive CD4+ T cell response.

Such a peptide is likely to be particularly useful in the treatment of hypersensitivity disorders. Hypersensitivity reactions include:

(i) allergies, resulting from inappropriate responses to innocuous foreign substances;
(ii) autoimmune diseases, resulting from responses to self tissue antigens; and
(iii) graft rejection, resulting from responses to a transplant.

Examples of allergies include, but are not limited to: hay fever, extrinsic asthma, insect bite and sting allergies, food and drug allergies, allergic rhinitis, bronchial asthma chronic bronchitis, anaphylactic syndrome, urticaria, angioedema, atopic dermatitis, allergic contact dermatitis, erythema nodosum, erythema multiforme, Stevens-Johnson Syndrome, rhinoconjunctivitis, conjunctivitis, cutaneous necrotizing venulitis, inflammatory lung disease and bullous skin diseases.

Examples of the autoimmune diseases include, but are not limited to: rheumatoid arthritis (RA), myasthenia gravis (MG), multiple sclerosis (MS), systemic lupus erythematosus (SLE), autoimmune thyroiditis (Hashimoto's thyroiditis), Graves' disease, inflammatory bowel disease, autoimmune uveoretinitis, polymyositis and certain types of diabetes, systemic vasculitis, polymyositis-dermatomyositis, systemic sclerosis (scleroderma), Sjogren's Syndrome, ankylosing spondylitis and related spondyloarthropathies, rheumatic fever, hypersensitivity pneumonitis, allergic bronchopulmonary aspergillosis, inorganic dust pneumoconioses, sarcoidosis, autoimmune hemolytic anemia, immunological platelet disorders, cryopathies such as cryofibrinogenemia and autoimmune polyendocrinopathies.

A variety of tissues are commonly transplanted in clinical medicine, including kidney, liver, heart lung, skin, cornea and bone marrow. All grafts except corneal and some bone marrow grafts usually require long-term immunosuppression at present.

In one embodiment of this aspect of the invention, the peptide is for use in the treatment and/or prevention of diabetes. In this embodiment, the peptide may be derivable from the target antigen IA2.

In a further embodiment of this aspect of the invention, the peptide is for use in the treatment and/or prevention of multiple sclerosis (MS). Multiple sclerosis (MS) is a chronic inflammatory disease characterised by multiple demyelinating lesions disseminated throughout the CNS white matter and occurring at various sites and times (McFarlin and McFarland, 1982 New England J. Medicine 307:1183-1188 and 1246-1251). MS is thought to be mediated by autoreactive T cells.

In this embodiment the peptide may be derivable from one of autoantigens, in particular myelin basic protein (MBP) or proteolipid protein (PLP). MBP is possibly more appropriate than PLP, because PLP is highly hydrophobic and peptides derived from it tend to clump together. MBP is immunogenic and MBP-specific T lymphocytes have encephalitogenic activity in animals (Segal et al., 1994 J. Neuroimmunol. 51:7-19; Voskuhl et al., 1993 J. Neuroimmunol 42:187-192; Zamvil et al., 1985 Nature 317:355-8).

In a preferred embodiment, the peptide is derivable from one of the immunodominant regions of MBP, namely: 1-24, 30-54, 75-99, 90-114, 105-129, 120-144, 135-159 and 150-170.

In an especially preferred embodiment the peptide is selected from one of the MBP peptides shown to act as APITOPEs by the present inventors, which include the following peptides: 30-44, 80-94, 83-99, 81-95, 82-96, 83-97, 84-98, 110-124, 130-144, 131-145, 132-146 and 133-147.

APITOPEs for MHC class I may be used, for example, to modify anti-viral CD8+ responses in a tolerogenic fashion.

Pharmaceutical Composition

The present inventors predict that, despite "bystander suppression" it may be necessary to target a number of different T cell clones in order to induce tolerance effectively. Hence a plurality of peptides may be administered to an individual in order to prevent or treat a disease.

In a third aspect, the present invention relates to a pharmaceutical composition comprising a plurality of APITOPEs.

The pharmaceutical composition may, for example comprise between 2 and 50 APITOPEs, preferably between 2 and 15 APITOPEs. The APITOPEs may be derivable from the same or different target antigen(s). Preferably the APITOPEs are either all able to bind to MHC class I, or all able to bind MHC class II, without further processing. In a preferred embodiment all the APITOPEs in the pharmaceutical composition are either able to bind to MHC class I or class II without further processing.

The pharmaceutical composition may be in the form of a kit, in which some or each of the APITOPEs are provided separately for simultaneous, separate or sequential administration.

Alternatively (or in addition) if the pharmaceutical composition (or any part thereof) is to be administered in multiple doses, each dose may be packaged separately.

The pharmaceutical composition may comprise a therapeutically or prophylactically effective amount of the or each APITOPE and optionally a pharmaceutically acceptable carrier, diluent or excipient.

Also, in the pharmaceutical compositions of the present invention, the or each APITOPE may be admixed with any suitable binder(s), lubricant(s), suspending agent(s), coating agent(s), or solubilizing agent(s).

Administration

The peptide should be administered in soluble form in the absence of adjuvant.

Preferably the peptide is administered by a mucosal route.

Studies have shown that peptide, when given in soluble form intraperitoneally (i.p.), intravenously (i.v.) or intranasally (i.n.) or orally can induce T cell tolerance (Anderton and Wraith (1998) as above; Liu and Wraith (1995) as above; Metzler and Wraith (1999) Immunology 97:257-263).

Preferably the peptide is administered intranasally.

Studies in mice have demonstrated that the duration of peptide administration required to induce tolerance depends on the precursor frequency of T cells in the recipient (Burkhart et al (1999) as above). In many experimental studies, it has been shown that repeated doses of peptide are required to induce tolerance (Burkhart et al (1999) as above). The exact dose and number of doses of peptide will therefore depend on the individual; however, in a preferred embodiment a plurality of doses is administered.

If a plurality of peptides is administered simultaneously, they may be in the form of a "cocktail" which is suitable for administration in single or multiple doses. Alternatively it may be preferably to give multiple doses but vary the relative concentrations of the peptides between doses.

In a preferred embodiment a "dose escalation" protocol may be followed, where a plurality of doses is given to the patient in ascending concentrations. Such an approach has been used, for example, for phospholipase A2 peptides in immunotherapeutic applications against bee venom allergy (Müller et al (1998) J. Allergy Clin Immunol. 101:747-754 and Akdis et al (1998) J. Clin. Invest. 102:98-106).

Myelin Basic Protein

A further aspect of the invention relates to a composition which comprises a plurality of peptides from myelin basic protein.

Myelin basic protein (MBP) is an 18.5 kDa protein isolatable from human brain white matter. The mature protein has 170 amino acids and the sequence is widely available in the literature (see for example: Chou et al (1986) J. Neurochem. 46:47-53, FIG. 1; Kamholz et al (1986), PNAS 83:4962-4966, FIG. 2; U.S. Pat. No. 5,817,629, SEQ ID NO: 1; Roth et al (1987), J. Neurosci. Res. 17:321-328, FIG. 4; Medeveczky et al (2006), FEBS Letters 580:545-552, FIG. 3B).

MBP Peptides

The peptides used in the composition and kit of the present invention may be made using chemical methods (Peptide Chemistry, A practical Textbook. Ibid). For example, peptides can be synthesized by solid phase techniques (Roberge J Y et al Ibid), cleaved from the resin, and purified by preparative high performance liquid chromatography (e.g., Creighton Ibid). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage from a longer polypeptide. For example, the peptide may be obtained by cleavage from full length MBP. The composition of a peptide may be confirmed by amino acid analysis or sequencing (e.g., the Edman degradation procedure).

The peptides used in the compositions and kits of the present invention are as follows:

MBP 30-44:

(SEQ ID NO: 1)
COOH-Pro-Arg-His-Arg-Asp-Thr-Gly-Ile-Leu-Asp-
Ser-Ile-Gly-Arg-Phe-NH2.

MBP 83-99:

(SEQ ID NO: 2)
COOH-Glu-Asn-Pro-Val-Val-His-Phe-Phe-Lys-Asn-
Ile-Val-Thr-Pro-Arg-Thr-Pro-NH2.

MBP 131-145:

(SEQ ID NO: 3)
COOH-Ala-Ser-Asp-Tyr-Lys-Ser-Ala-His-Lys-Gly-
Phe-Lys-Gly-Val-Asp-NH2.

MBP 140-154:

(SEQ ID NO: 4)
COOH-Gly-Phe-Lys-Gly-Val-Asp-Ala-Gln-Gly-Thr-
Leu-Ser-Lys-Ile-Phe-NH2.

The terms "MBP 30-44", "MBP 83-99", "MBP 131-145" and "MBP 140-154" encompass modified peptides. For example the peptides may be mutated, by amino acid insertion, deletion or substitution, so long as the MHC binding-specificity of the unmodified peptide is retained, together with its capacity to be presented to a T cell. The peptide may, for example, have 5, 4, 3, 2, 1 or 0 mutations from the unmodified sequence.

Alternatively (or in addition) modifications may be made without changing the amino acid sequence of the peptide. For example, D-amino acids or other unnatural amino acids can be included, the normal amide bond can be replaced by ester or alkyl backbone bonds, N- or C-alkyl substituents, side chain modifications, and constraints such as disulphide bridges and side chain amide or ester linkages can be included. Such changes may result in greater in vivo stability of the peptide, and a longer biological lifetime.

Modification of epitopes may be performed based on predictions for more efficient T-cell induction derived using the program "Peptide Binding Predictions" devised by K. Parker (NIH) which may be found at http://www-bimas.dcrt.nih.gov/cgi-bin/molbio/ken_parker_comboform (see also Parker, K. C et al. 1994. J. Immunol. 152:163).

MBP peptides may be formulated into the composition as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2 ethylamino ethanol, histidine and procaine.

Composition

The composition of the present invention may be for prophylactic or therapeutic use.

The composition may by prepared as an injectable, either as liquid solution or suspension; solid form suitable for solution in, or suspension in, liquid prior to injection may also be prepared. The preparation may also be emulsified, or the protein encapsulated in liposomes. The active ingredients may be mixed with excipients which are pharmaceutically acceptable and compatible with the active ingredient. Suitable excipients are, for example, water, saline (for example, phosphate-buffered saline), dextrose, glycerol, ethanol, or the like and combinations thereof.

In addition, if desired, the composition may contain minor amounts of auxiliary substances such as wetting or emulsifying agents and/or pH buffering agents.

In the composition, the relative ratio of the peptides (MBP 30-44:MBP 83-99:MBP 131-145:MBP 140-154) may be approximately 1:1:1:1. Alternatively the relative ratios of each peptide may be altered, for example, to focus the tolerogenic response on a particular sub-set of autoreactive T-cells.

After formulation, the composition may be incorporated into a sterile container which is then sealed and stored at a low temperature, for example 4° C., or it may be lyophilized (freeze-dried). Lyophilisation may permit long-term storage in a stabilised form. The composition may require bulking agents such as mannitol, dextran or glycine, prior to lyophilization. Examples of lyophilization of biologicals can be found in "Effect of formulation on lyophilization" http://wwwdevicelink.com/ivdt/archive/97/01/006.html and Cheman and Corona, (2006) Report in Bioprocessing and Biopartnering. P. 20-21. Phosphate, citrate or acetate may be used as buffering salts. HCl or NaOH may be used for pH adjustment. Disaccharides such as sucrose or trehalose may be used to aid in the stabilization of the composition.

The composition may be administered in a convenient manner such as by the oral, intravenous (where water soluble), intramuscular, subcutaneous, intranasal, intradermal or suppository routes or implanting (e.g. using slow release molecules).

The composition may advantageously be administered via intranasal, subcutaneous or intradermal routes.

The method and pharmaceutical composition of the invention may be used to treat a human subject. Typically, a physician will determine the actual dosage which will be most suitable for an individual subject and it will vary with the age, weight and response of the particular patient.

In a preferred embodiment a "dose escalation" protocol may be followed, where a plurality of doses is given to the patient in ascending concentrations. Such an approach has been used, for example, for phospholipase A2 peptides in immunotherapeutic applications against bee venom allergy (Müller et al (1998) J. Allergy Clin Immunol. 101:747-754 and Akdis et al (1998) J. Clin. Invest. 102:98-106).

Kits

Conveniently, the four MBP peptides may be administered together, in the form of a mixed composition or cocktail. However, there may be circumstances in which it is preferable to provide the peptides separately in the form of a kit, for simultaneous, separate, sequential or combined administration.

For example, the kit may comprise the four peptides in separate containers, or two containers, each comprising two peptides. The contents of the containers may or may not be combined prior to administration.

The kit may also comprise mixing and/or administration means (for example a vaporiser for intranasal administration; or a syringe and needle for subcutaneous/intradermal dosing). The kit may also comprise instructions for use.

The pharmaceutical composition or kit of the invention may be used to treat and/or prevent a disease.

In particular, the composition/kit may be used to treat and/or prevent multiple sclerosis and/or optical neuritis.

Multiple Sclerosis

Multiple Sclerosis (MS) is the most common neurological disorder among young adults (20 to 40 years old) affecting around 385,000 people in Europe and 300,000 in the USA. It is a chronic degenerative disease of the central nervous system in which gradual destruction of myelin occurs in patches throughout the brain and/or spinal cord, interfering with neural connectivity and causing muscular weakness, loss of coordination and speech and visual disturbances.

After 10 years, about half of the individuals who are initially diagnosed with Relapsing-Remitting MS (RRMS) find that the frequency of relapses decreases but disability increases. This is known as Secondary Progressive MS (SPMS). Some estimates are that within 25 years, about 90% of people with RRMS will progress to the secondary-progressive type. As with RRMS, Secondary Progressive MS can vary widely. For some patients, the increase or progression of disability is very gradual, and for others it can occur more quickly. In general however, recovery from attacks become less and less complete, and symptoms tend to increase and disability grows. Clinical attacks become less pronounced and remissions tend to disappear, but more CNS tissue has now been destroyed and the cumulative damage is more apparent on MRI's.

The composition of the invention may be used to treat a patient with recent-onset MS, RRMS or SPMS.

The composition of the present invention may reduce or ameliorate one or more of the symptoms of MS, which include reduced or loss of vision, stumbling and uneven gait, slurred speech, urinary frequency and incontinence, mood changes and depression. SPMS can be associated with muscle spasms and severe paralysis.

In particular the composition may ameliorate optical neuritis.

Optic Neuritis

Optic Neuritis (ON) is an inflammation, with accompanying demyelination, of the optic nerve serving the retina of the eye. It is a variable condition and can present with any of the following symptoms: blurring of vision, loss of visual acuity, loss of some or all colour vision, complete or partial blindness and pain behind the eye.

Optic Neuritis is one of the most frequently presenting symptoms of multiple sclerosis and is the most common symptom at onset of MS. ON can, however, be attributable to causes other than MS, such as ischemic optic neuropathy. ON presents unilaterally (in one eye only) in 70% of cases.

Most typically, Optic Neuritis first affects people aged between 15 and 50 years of age. In this age group, studies indicate that more than 50% of patients will convert to Multiple Sclerosis within 15 years. As with MS, women are about twice as likely as men to present with ON and the prevalence in Caucasian peoples is higher than in other racial groups.

The main symptoms of Optic Neuritis are:

Loss of visual acuity (blurring of vision).
Eye pain.
Dyschromatopsia (reduced colour vision).
Movement and sound phosphenes (visual flashing sensations brought about by side-to-side eye movement or sound).
Uhthoff's symptom, the worsening of symptoms with heat or exhaustion.

Treatment of ON with a composition according to the present invention may prevent, reduce or ameliorate any of these symptoms. In order to monitor progression of ON, visual acuity may conveniently be measured using a Snellens chart.

EXAMPLES

The following examples serve to illustrate the present invention, but should not be construed as a limitation thereof. The invention particularly relates to the specific embodiments described in these examples For the purpose of the Examples, the following names may be used for the MBP peptides:

| MBP peptide | Name in Examples (interchangeable) | |
|---|---|---|
| 30-44 | ATX-MS-01 | APITOPE MS1 |
| 83-99 | ATX-MS-07 | APITOPE MS7 |
| 131-145 | ATX-MS-04 | APITOPE MS4 |
| 140-154 | ATX-MS-06 | APITOPE MS6 |

The composition of four peptides is termed ATX-MS-1467

Example 1

Identification of T Cell Epitopes in MBP

Materials and Methods

Antigens

Human MBP is prepared from brain white matter as described by Deibler et al. (Deibler et al., 1972 Preparative Biochemistry 2:139), and its purity assessed by SDS-PAGE. MBP and *Mycobacterium tuberculosis* purified protein derivative (PPD) (UK Central Veterinary Laboratory, Surrey) are used in proliferative assays at previously determined optimal concentrations; the optimum concentration for each antigen is 50 µg/ml. A panel of 15-mer overlapping peptides spanning the whole MBP molecule are synthesized using standard F-moc chemistry on an Abimed AMS 422 multiple peptide synthesizer (Abimed, Langenfeld, Germany). Each peptide is displaced by 5 a.a. and overlapped by 10 a.a. We produce 33 peptides that are pooled into groups of 3 and pools are tested at the optimum concentration of 50 µg/ml, such that in vitro each peptide is present at a concentration of 16.6 µg/ml.

Patients and Control Subjects

The subjects of this study consist of 12 patients with clinically definite or laboratory supported definite MS (Poser et al., 1983), with an age range of 29-51 years. Eight of the 12 patients are involved in a trial of interferon-β; otherwise all other MS patients have received no corticosteroid treatment for at least 3 months prior to the commencement of the study. The control group consisted of 13 healthy individuals with an age range of 25-55 years, and none have received immunosuppressive therapy for at least 3 months prior to the blood sample being obtained.

Tissue Culture Medium

RPMI-1640 medium supplemented with 20 mM HEPES (Sigma, Poole, UK), penicillin (100 U/ml), streptomycin sulphate (100 mg/ml), and 4 mM L-glutamine (all from Life Technologies, Paisley, Scotland), is used as the tissue culture medium. Medium without serum is used for washing lymphoid cells and TCL. For all culture conditions and assays, medium is supplemented with 10% heat inactivated autologous plasma.

Culture Conditions and T Cell Proliferative Assays

Citrated peripheral blood (50-100 ml) is collected by venepuncture from each subject after informed written consent had been obtained. Peripheral blood mononuclear cells (PBMC) are isolated from blood by density centrifugation on Histopaque-1077 (Sigma, Poole, UK), and cultured in 1.5 ml volumes in 24-well tissue culture plates (Nunc International, Costar, Corning Inc. New York, USA) at a concentration of $1 \times 10^6$ cells per ml, containing either PPD, MBP or peptides of MBP. The plates are incubated at 37° C. in a humidified atmosphere of 5% $CO_2$/95% air. Between days 5 and 14 duplicate aliquots of 100 µl are withdrawn from each culture, transferred to a 96-well round bottom microtitre plate and pulsed with 0.4 µCi [$^3$H]-Thymidine (Amersham International, Amersham, UK). After 18 hours cells are harvested onto glass fiber mats (LKB-Wallac, Turku, Finland) using a Mach 111 harvester 96 (Tomtec, Orange, N.J., USA). [$^3$H]-Thymidine incorporation is determined using a Microbeta liquid scintillation counter (LKB-Wallac). Test wells containing antigen are considered positive when the δcpm>1000 and the Stimulation Index (SI)>3, where SI=CPM antigen containing culture/CPM culture without antigen.

Generation of T Cell Lines and T Cell Clones

MBP-specific T cell lines (TCL) are generated from 8 MS patients and 2 healthy control donors. PBMC from each subject are separated as described above and plated out at $1 \times 10^6$ cells/ml in 6-well plates in the presence of MBP (50 μg/ml); a portion of PBMC from each subject is regularly frozen and stored for subsequent restimulations. Seven days later the cells are fed with fresh medium containing 2% IL-2 (Lymphocult-HT; Biotest LTD., Birmingham, UK), and on day 12 of culture all cells are restimulated with antigen, IL-2 and irradiated (2500 Rad) autologous PBMC as a source of antigen presenting cells (APC), at a cell ratio of IT cell:5 APC. Cells are expanded in IL-2 every 3-4 days, and on day 14 are restimulated with antigen, IL-2 and PBMC, as described above. On the day of the first restimulation cells are examined for specific proliferation to MBP. Briefly, $2 \times 10^4$ T cells and $1 \times 10^5$ irradiated autologous PBMC are cultured in triplicate, in 96-well round-bottom plates, in the presence of MBP. Cells are cultured for 2 days and pulsed with (3H)-Thymidine at 0.4 μCi/well during the last 18 hours of the culture. Cells are then harvested as described above, and a TCL is considered to be MBP-specific with a δcpm>1000 and a SI>3.

Following 3 restimulation/expansion cycles TCL are cloned using PHA (Sigma, Poole, Dorset, UK)) in the presence of autologous irradiated PBMC as APC. T cells are plated under limiting dilution conditions at 0.1 cell/well, 0.3 cell/well and 1 cell/well and cultured in Terasaki plates (Nunc International, Costar) with $1 \times 10^4$ irradiated PBMC, 5 μg/ml PHA, and 2% IL-2. After 10-12 days, growth-positive wells are expanded onto 96-well round-bottom plates, using $1 \times 10^5$ irradiated PBMC, 5 μg/ml PHA and IL-2. Three days later wells are fed with fresh medium containing IL-2, and on day 7 the clones are expanded onto 48-well plates using $5 \times 10^5$ irradiated PBMC, PHA and IL-2; at this point clones are tested in proliferation assays for specific responses to MBP. MBP-specific clones are expanded a week later onto 24-well plates, using $1 \times 10^6$ irradiated PBMC with PHA or Dynabeads (Dynal, UK) and IL-2. The clones are maintained in 24-well plates using a 7-10 day restimulation/expansion cycle, essentially as described above. The ability of T cell clones (TCC) to recognize the panel of MBP peptides is tested by proliferation assays, as described above.

Results

MBP-Peptide Recognition Amongst MS Patients and Healthy Individuals

Figure 1B:
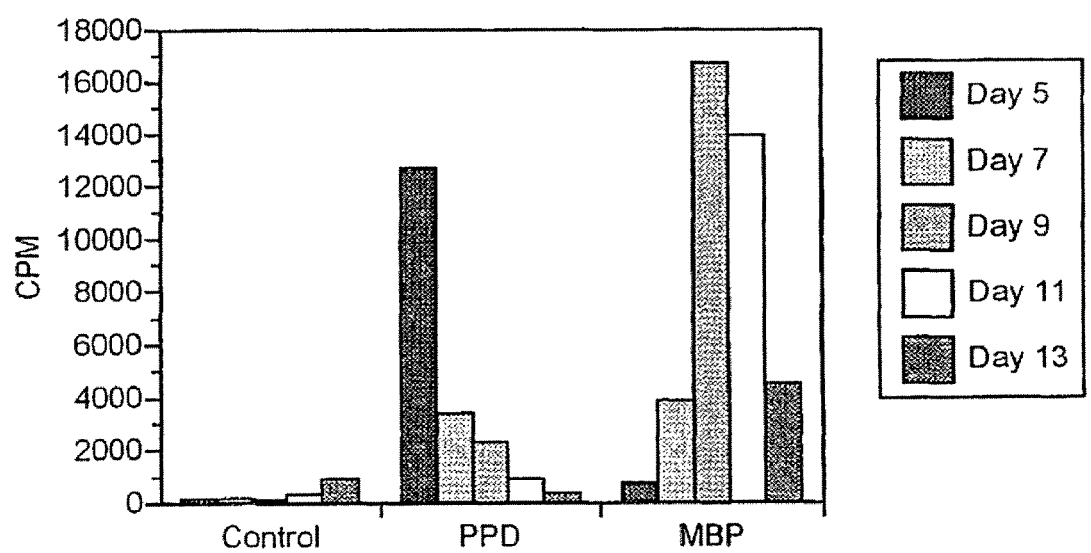

The present inventors use a kinetic response assay in which PBMC from MS patients and healthy subjects are tested for their ability to respond to a panel of overlapping 15-mer synthetic peptides spanning the full length of human MBP. The proliferative response of PBMC from each culture is examined at 5 time points over a period of 2 weeks, and the kinetic profile of the response to MBP and peptides is compared with the response to PPD, the latter representing a secondary response/memory antigen. No significant difference is found in the PBMC response to MBP and/or peptides between patients on Interferon-P and those on no treatment (data not shown). The response to MBP in both MS patients and healthy controls peaked later than the response to PPD, thereby following the kinetic characteristics of the response to a non-recall antigen. FIG. 1 shows a typical example of the kinetic profile to PPD and MBP in MS patients and healthy individuals.

As shown in FIG. 2, the two peptides most commonly recognised by MS patients are 90-114 and 75-99 (6/12 patients each), followed by regions 30-54, 135-159 and 150-170 (5/12 patients), and 1-24 and 105-129 (4/12 patients). Three patients respond to a.a. 15-39 and 120-144. Two patients recognise 45-69, and none of the MS patients respond to region 60-84.

According to FIG. 10, where all the patients are HLA-DR2 positive, the two peptides most commonly recognised by MS patients are 90-114 and 75-99 (6/11 patients each), followed by regions 120-144, 135-159 and 150-170 (5/11 patients), and 1-24, 15-39, 30-54 and 105-129 (4/11 patients). Three patients respond to a.a. 45-69, and again none of the MS patients respond to region 60-84.

Figure 3:
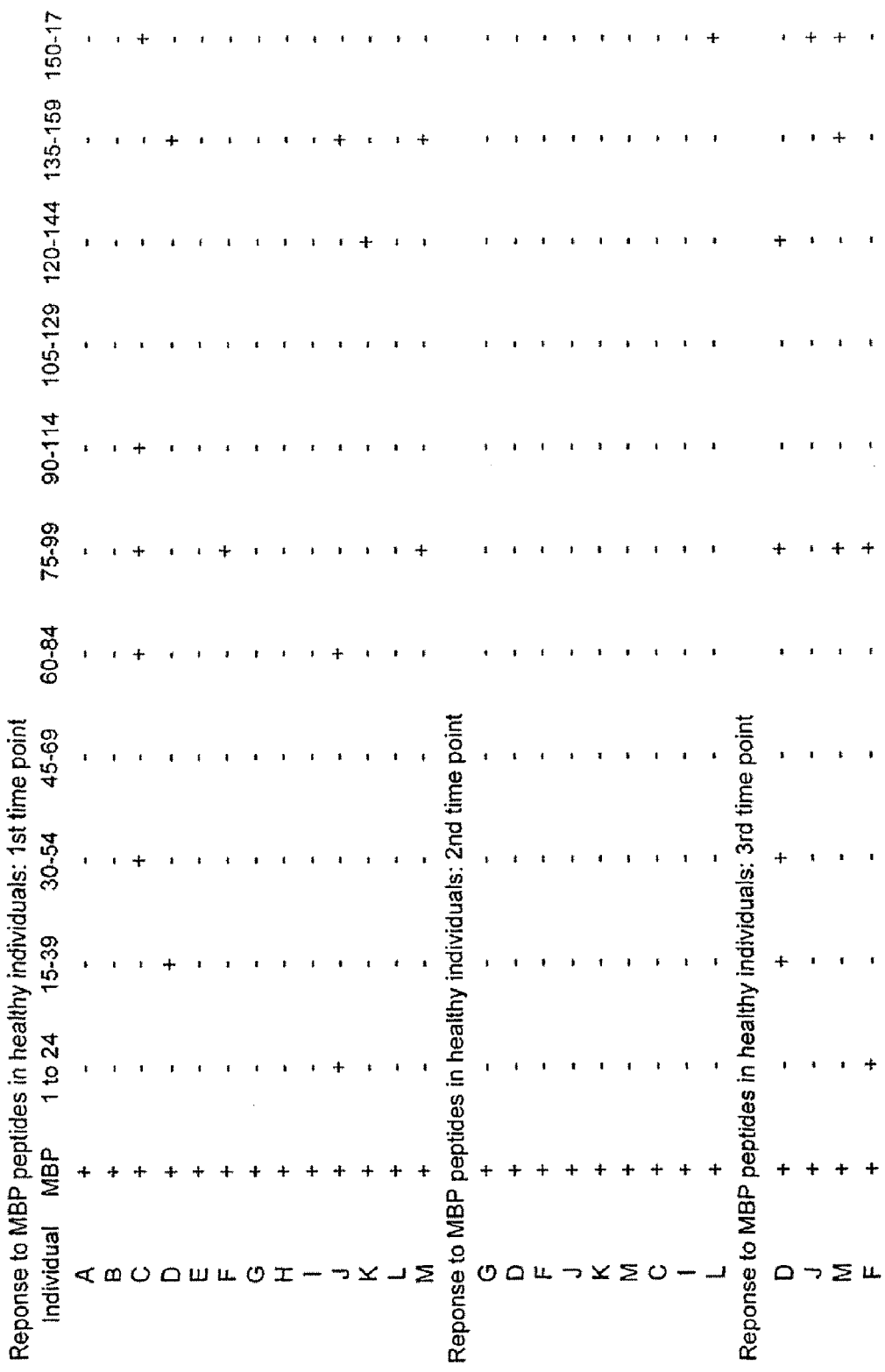
FIG. 3 is a table which summarises PBMC responses to MBP and MBP-peptides in healthy individuals. Between 4 and 7 months elapsed between each time point.

By contrast, healthy individuals recognise significantly fewer peptides, with only 2 control subjects responding to more than 2 peptides (C and J; FIG. 3). Control individuals C and J are the only two who recognise a.a. 60-84, a region not seen by this group of patients. Interestingly both these individuals express the DRB1* 0701 allele. Regions 45-69 and 105-129 are not recognised by any of the healthy donors, whereas 75-99 and 150-170 are recognised by 4 healthy individuals; 135-159 is recognised by three healthy individuals; 1-24, 30-54, 60-84 and 120-144 is recognised by two healthy individuals; and 15-39 and 90-114 are recognised by one individual. Overall, 8/13 healthy individuals do not respond to any of the overlapping peptides, whereas only 1/12 MS patients (MS 19) consistently fail to recognise the MBP peptides. Notably this patient is unique in not responding to MBP protein.

FIG. 11 also shows the response of healthy individuals to MBP peptides. In this study, only 1 control subject responds to more than 2 peptides (N11). N11 is also the only individual who recognizes a.a. 60-84, a region not seen by this group of patients. Regions 15-39, 45-69 and 105-129 are not recognised by any of the healthy donors, whereas 120-144 and 135-159 are recognised by two healthy individuals; and 1-24, 30-54, 60-84, 75-99, 90-114 and 150-170 are recognised by one individual. Overall, 9/12 healthy individuals do not respond to any of the overlapping peptides.

Overall, the day on which the response to MBP and/or peptides peaked did not differ significantly between healthy individuals and patients, and the kinetics in both groups resembled those of a primary antigenic response. In addition, the magnitude of the response to MBP and peptides did not differ between patients and healthy individuals.

MBP-Peptide Recognition Changes Over Time

Having established that patients with MS respond to a broad spectrum of MBP peptides, the present inventors decided to examine whether PBMC recognition in the same individuals is focused and stable over the course of approximately 4-12 months. As shown in FIGS. 2, 10 and 3 neither the MS patients nor the healthy individuals exhibited the same peptide recognition pattern.

Figure 4A:
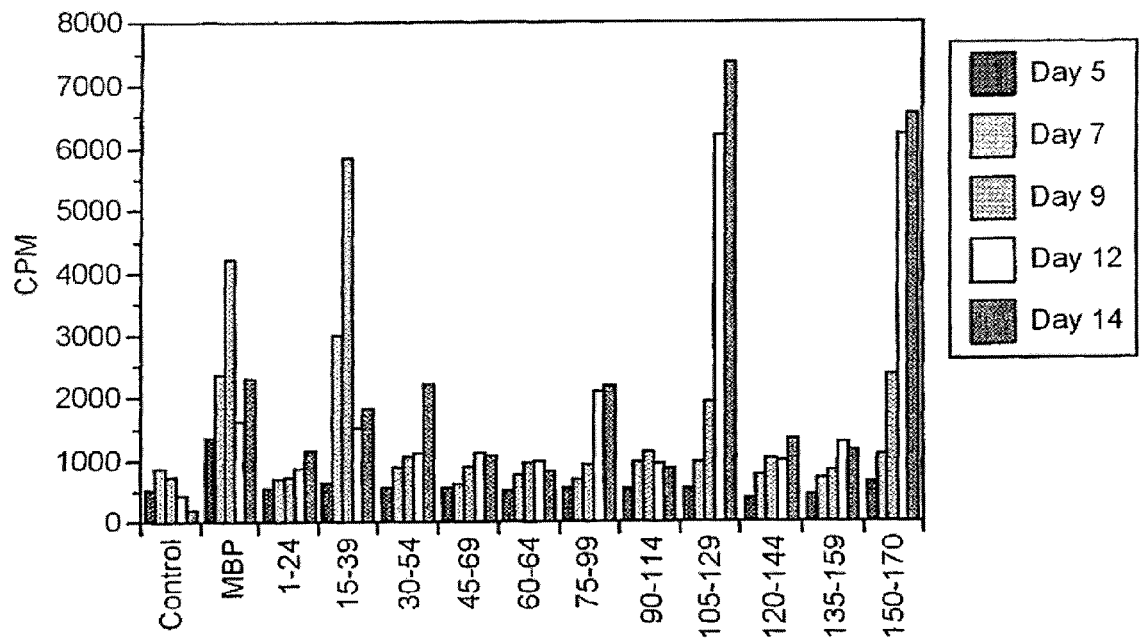
FIG. 4 shows an example of an MS patient (MS 49) who responds to multiple peptides at 2 different time points (A; first time point and B; second time point), but for whom the recognition profile during the second time point (B), measured 4 months later, differs significantly. PBMC were cultured in the presence of MBP and a panel of peptides spanning the full length of MBP, and proliferation was measured by 3H-thymidine uptake. The broad T-cell proliferative response observed at the first time point was significantly different to the response measured 4 months later (B; second time point).
Figure 4B:
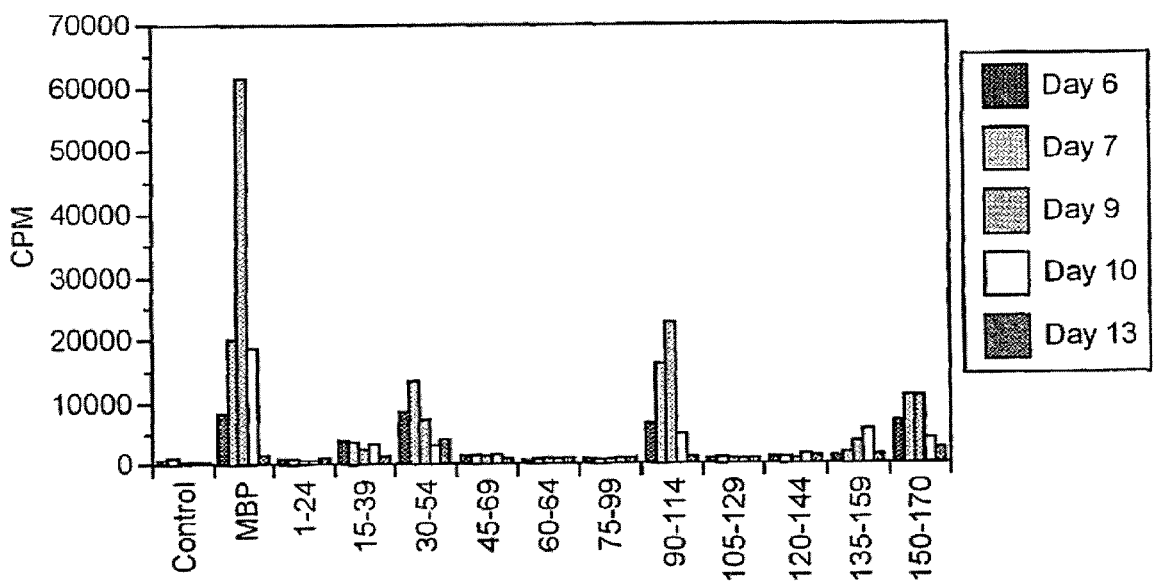

FIG. 4 represents an example of an MS patient (MS 49) who responds to multiple peptides at 2 different time points, but the recognition profile during the second time point, measured 4 months later, differs significantly. That is, in the second kinetic assay the PBMC response to a.a. 15-39, 30-54 and 150-170 persists, however the response to 75-99 and 105-129 regresses and shifts to regions 90-114 and 135-159.

Figure 5A:
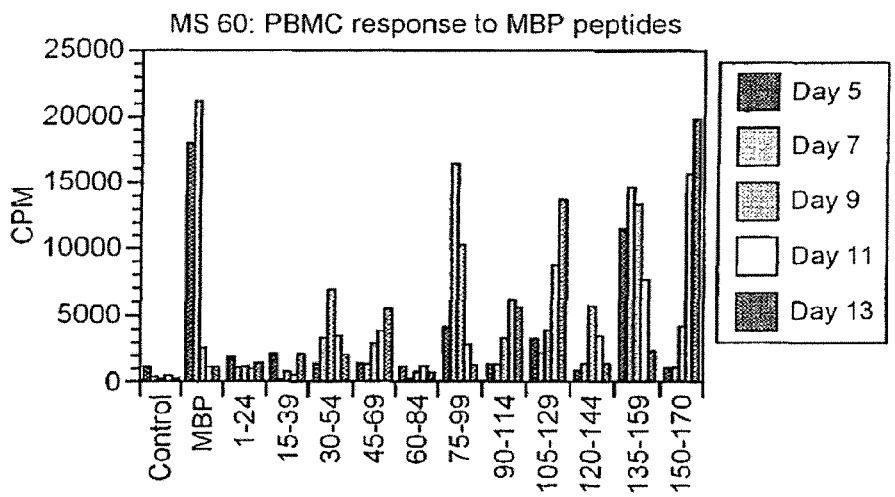
FIG. 5 shows an example of a patient whose broad epitope response (A; first time point) regresses (B; second time point) and reappears over a twelve-month period (C; third time point).
Figure 5B:
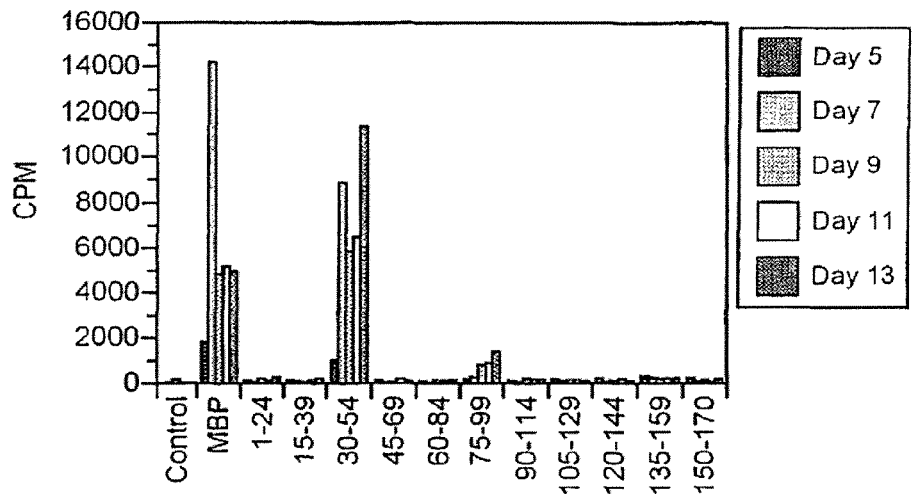
Figure 5C:
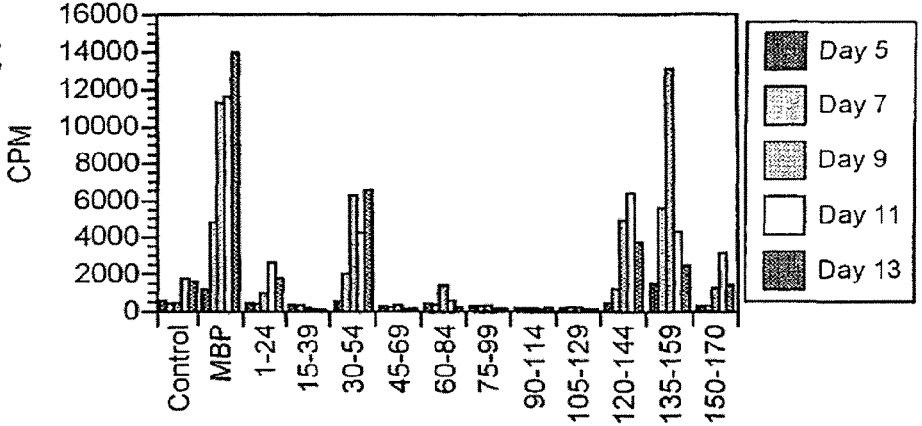

FIG. 5 (MS 60) illustrates an example of a patient whose broad epitope response regressed to a focused response over the period of 4 months. The healthy individuals who are tested the second time round fail to respond to any of the peptides (FIG. 3).

Overall the results demonstrate that patients with MS do not exhibit set patterns of recognition. Within each patient the PBMC response to several peptides can persist, regress, and shift to new regions of MBP, as seen in patient MS 49.

Cycling of Peptide Recognition

When the PBMC response to peptides is analyzed at 3 or more different time points over a period of 12 months, it becomes clear that in certain patients epitope recognition appears to fluctuate rather than shift irreversibly to new peptide regions. For example, as shown in FIGS. 2 and 10, patient MS 60 exhibits a cycling pattern of recognition to a.a. 120-144 and 135-159; that is, residues 120-144 and 135-159 are amongst many recognised at the first time point tested, the response to these 2 regions regresses by the second time point and then reappears at the third time point measured 4 months later. The kinetic profile of patient MS 41 demonstrates, similarly, that recognition of a.a. 135-159 fluctuates over several time points (see FIGS. 2 and 10).

Amongst the healthy control group (FIG. 3), one individual (M) exhibits a fluctuating response to regions 75-99 and 135-159, a second individual (F) recognizes 75-99 at two of the three time points analyzed, whilst a third subject (D) shows a cyclical response to residue 15-39.

Fine Mapping the Response to MBP

TCC are generated from 8 MS patients and 2 healthy individuals, and used to clarify the fine specificity of the peptide regions identified in the kinetic response assay. The specificity of each TCC is tested by its proliferative response to the panel of 15-mer peptides. Clone SD:A7 recognised region 1-24, and within this region this TCC responded to a.a. 5-19. Region 30-54 is recognised by 4 clones (MS49:D3, MS49:C8, MS49:A8, MS49:B6) and the epitope within this region is 30-44. One clone (MS39:D7) from an MS patient recognizes peptide 60-74, and interestingly one healthy individual responds to this region (60-84) in our kinetic response assay. Five clones (MS43:A7, MS41:B6, MS41:A2, MS41:C6, N5:8) recognize a.a. 83-99 which is contained in region 75-99. One patient produced TCC specific for a.a. 110-124 (MS60:A2, MS60:B3), contained within the 105-129 pool, and another TCC from the same patient is specific to 130-144 (MS60:E1), found within the 120-144 region. Five individuals produce clones which recognize epitopes within the region 135-159: MS60:F7, MS60:D1, MS59:F1 and N5:19 recognizes a.a. 140-154; MS57:A1 is specific to 140-149, and TCC MS17:A3 responds to sequence 130-144. This panel of clones clearly demonstrates the presence of at least 2 T cell epitopes within the 135-159 region of MBP. Lastly, region 150-170 is recognized by 2 clones specific to a.a. 156-169. The specificity of all TCC is summarized in FIG. 6.

Example 2

Identification of APITOPEs in MBP

Materials and Methods
Antigen-Presentation Assay Using an APIPS

Presentation of the peptides to T cell clones is measured by proliferation. APC are fixed in 0.5% paraformaldehyde and plated at $1 \times 10^5$ cells per well of a 96-well tissue culture plate. T cells clones are plated at $2 \times 10^4$ cells per well in the presence of varying concentrations of peptide. After incubation for 48 h at 37° C., proliferation is measured by [$^3$H] thymidine incorporation over 16-20 h. Results are compared with the ability of T cells to respond to the epitope presented by live APC.

Presentation of peptides to T cells isolated from DR2:MBP82-100 transgenic mouse was essentially as described above except APC were plated at $5 \times 10^5$ cells per well, T cells were plated at $1 \times 10^5$ cells per well, and incubation was allowed to proceed for 72 h prior to the addition of [$^3$H]-thymidine.

Results

In this experiment, peptides which have been identified as epitopes in the previous example are examined for their capacity to be presented using an APIPS. The results are shown in FIG. 7b. Of the five epitopes examined so far, four were found to be APITOPEs (30-44, 80-94, 110-124 and 130-144) and one was found to act as an epitope but not an APITOPE (156-170).

Example 2A

Investigation of MBP Peptides 30-44, 110-124, 130-144 and 156-170

In order to investigate whether various MBP peptides are APITOPEs, their capacity to be presented to T-cells by fixed APC is investigated. Live or pre-pulsed Mgar (HLA-DR2+ve) cells are pre-pulsed with the peptide in serum, or serum alone for 3.5 hours. Excess peptide is then removed from cells and the appropriate T cell clone added. The T cell proliferative response is measured by $^3$H-thymidine uptake.

Figure 8A:
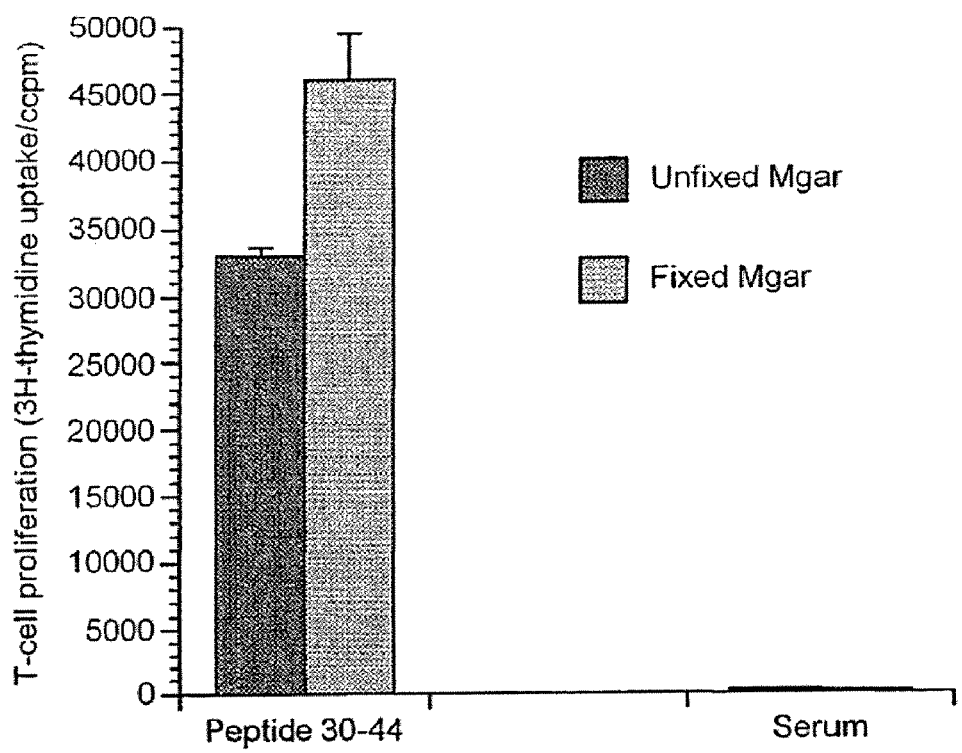
FIG. 8 shows the presentation of MBP peptide 30-44 (A) and MBP peptide 110-124 (B) to T cell clones by live and fixed APC.
Figure 8B:
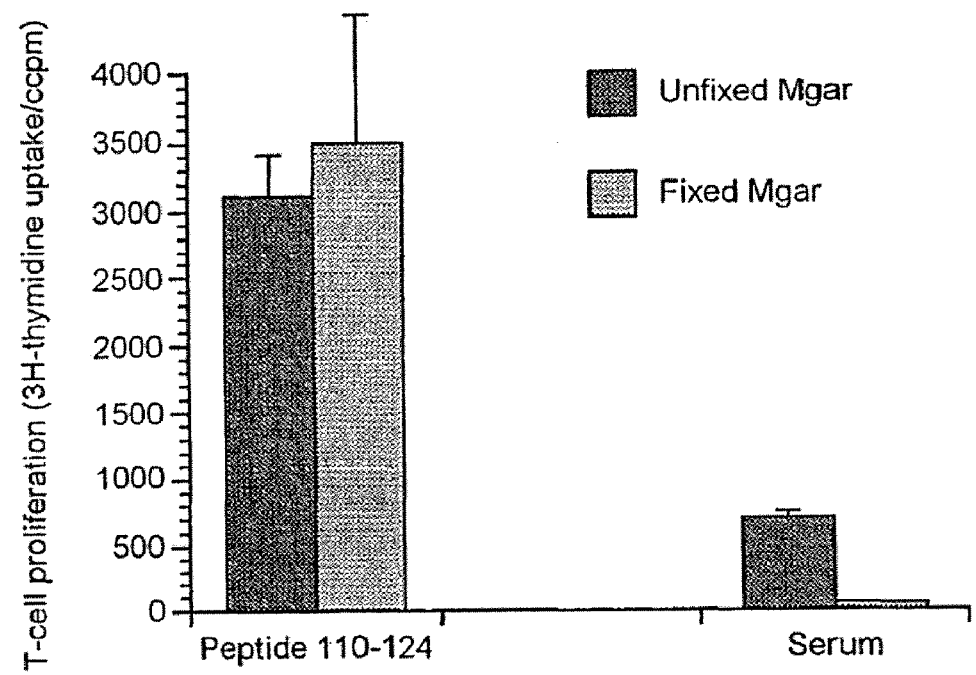
Figure 9A:
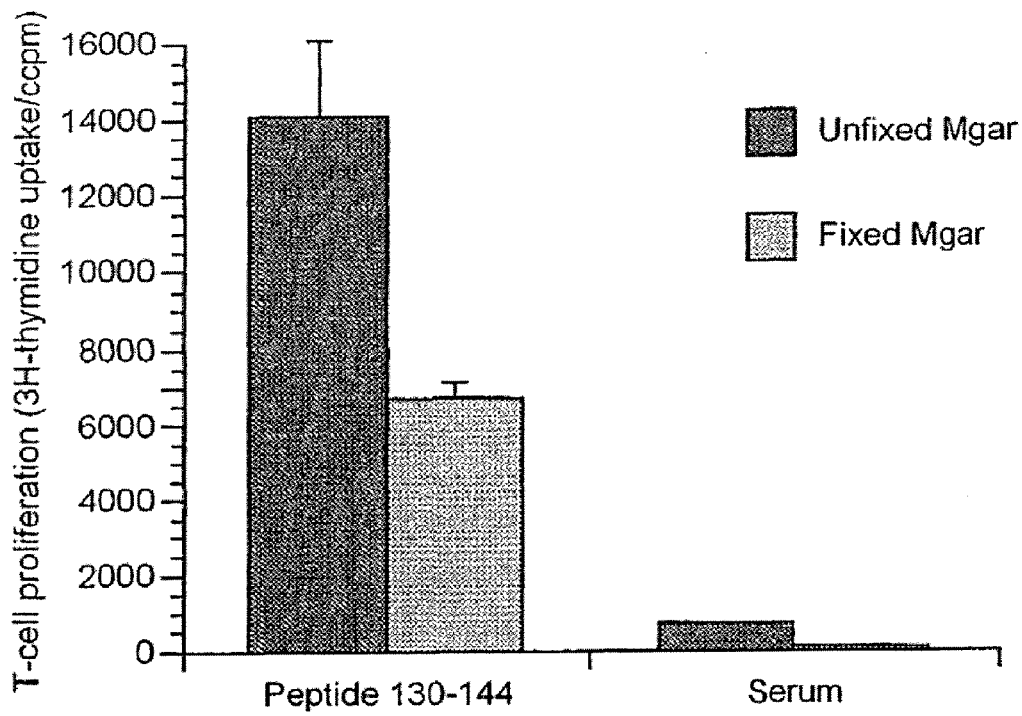
FIG. 9 shows the presentation of MBP peptide 130-144 (A) and MBP peptide 156-170 (B) to T cell clones by live and fixed APC.
Figure 9B:
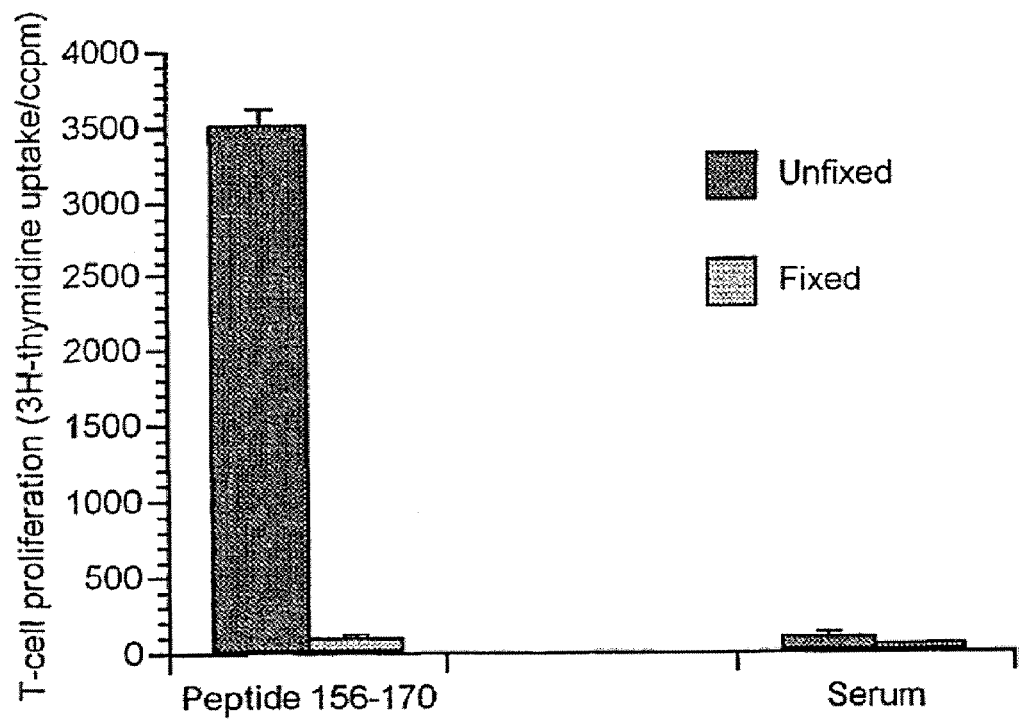

As shown in FIGS. 8 and 9, peptides 30-44 (FIG. 8A), 110-124 (FIG. 8B), and 130-144 (FIG. 9A) can be presented by fixed APC without further processing. These peptides are therefore defined as APITOPEs. Peptide 156-170, on the other hand, requires further processing for presentation to T cells (FIG. 9B). Fixed APC are unable to present this epitope to T cells, so 156-170 is not an APITOPE.

Example 2B

Identification of APITOPEs within the Regions 77-100 and 125-148 of MBP

Figure 12:
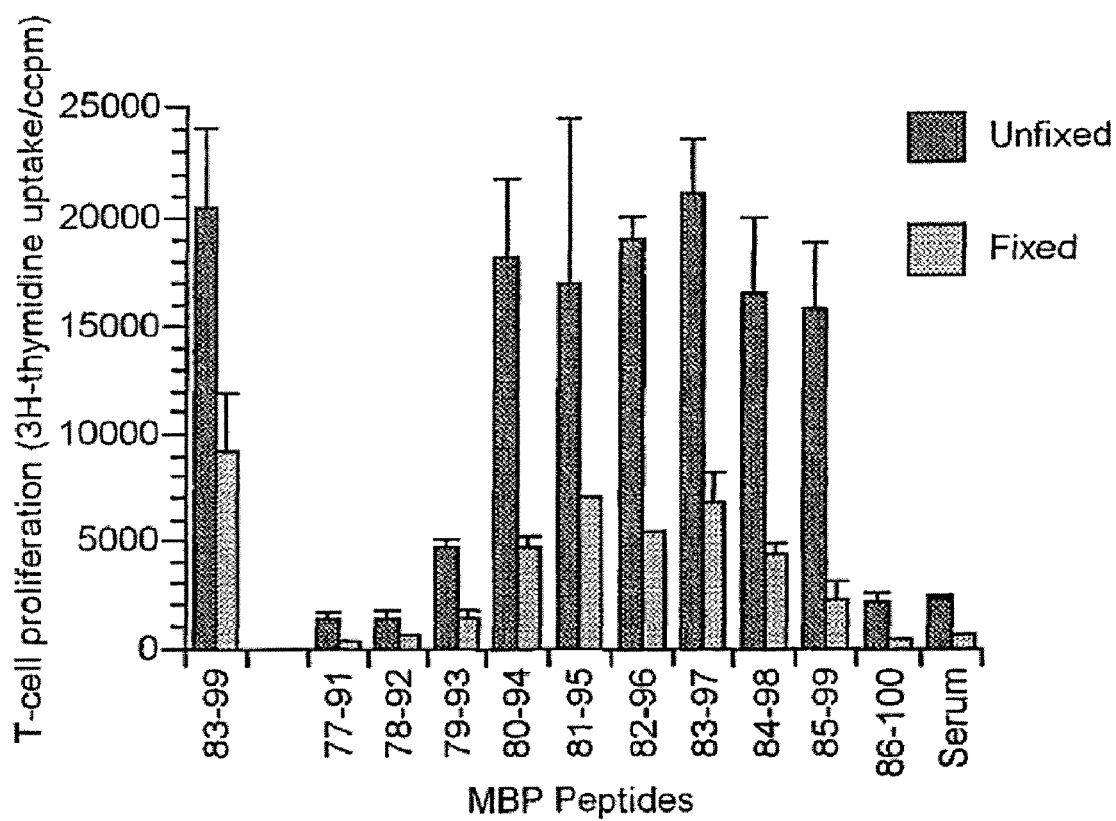
FIG. 12 shows the response of T-cells isolated from a DR2:MBP 82-100 transgenic mouse to presentation of nested MBP peptides in the region 77-100 by APC.
Figure 13:
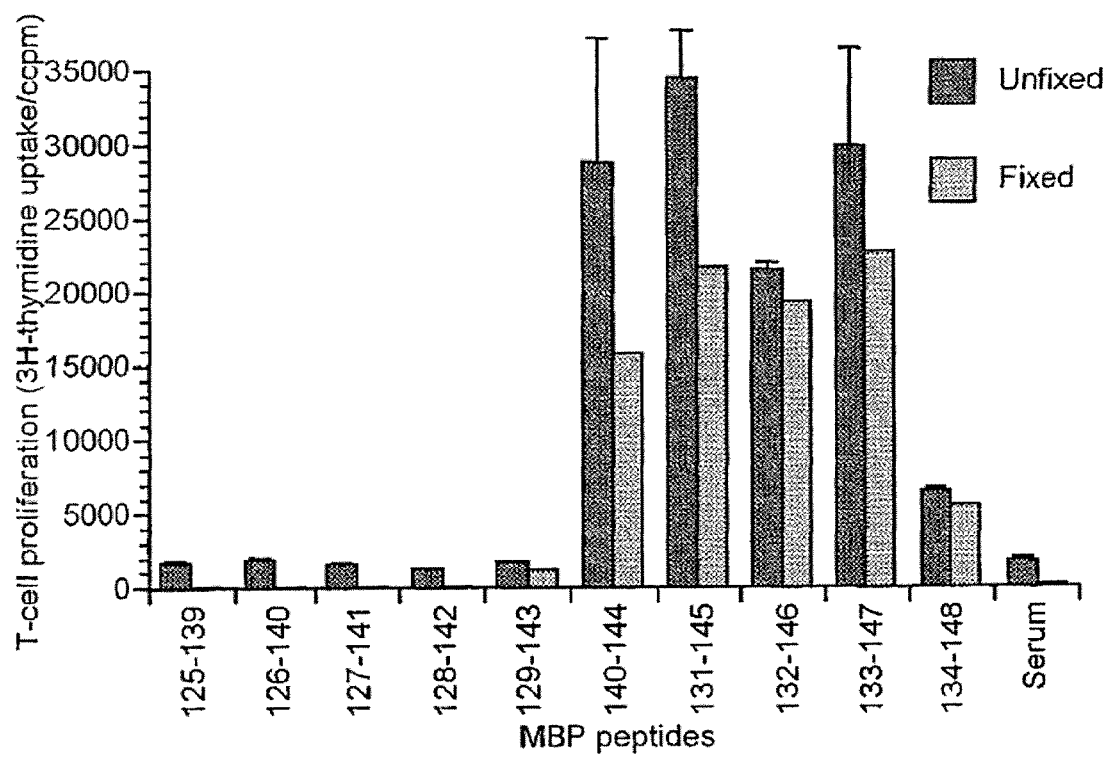
FIG. 13 shows the response of T cell clone MS17:A3 to presentation of nested MBP peptides in the region 125-148 by APC.

For any given epitope, there may exist one or more APITOPEs, capable of being presented to APC without further processing. The presence of APITOPEs within two regions of MBP is investigated by incubating live or p-formaldehyde-fixed Mgar (HLA-DR2+ve) cells are incubated with overlapping peptides in serum from MBP regions 77-100 (FIG. 12) and 125-148 (FIG. 13) or in serum alone. T cells were added and after 72 h (FIG. 12) or after 48 h (FIG. 13) the T cell proliferative response was measured by $^3$H-thymidine uptake. For MBP 77-100, the T cells are isolated from a DR2:MBP 82-100 transgenic mouse, whereas for MBP 130-144 the T cell clone MS17:A3 is used.

For MBP region 77-100 the following peptides are defined as APITOPEs:

| MBP 83-99 | ENPVVHFFKNIVTPRTP | (SEQ ID NO: 5) |
| MBP 80-94 | TQDENPVVHFFKNIV | (SEQ ID NO: 6) |
| MBP 81-95 | QDENPVVHFFKNIVT | (SEQ ID NO: 7) |
| MBP 82-96 | DENPVVHFFKNIVTP | (SEQ ID NO: 8) |
| MBP 83-97 | ENPVVHFFKNIVTPR | (SEQ ID NO: 9) |

-continued

```
MBP 84-98    MPVVHFFKNIVTPRT       (SEQ ID NO: 10)
```

The minimum MBP sequence recognised by T cells from DR2MBP 82-100 transgenic mouse is region 85-94.

For MBP region 125-148 the following peptides are defined as APITOPEs:

```
MBP 130-144  RASDYKSAHKGFKGV       (SEQ ID NO: 11)

MBP 131-145  ASDYKSAHKGFKGVD       (SEQ ID NO: 12)

MBP 132-146  SDYKSAHKGFKGVDA       (SEQ ID NO: 13)

MBP 133-147  DYKSAHKGFKGVDAQ.      (SEQ ID NO: 14)
```

The minimum MBP sequence recognised by T-cell clone MS17:A3 is region 133-144.

Example 2C

Investigation of Region 89-101 of MBP

The present inventors have previously shown that, in contrast to other myelin T cell epitopes, administration of peptide 89-101 in soluble form does not prevent murine experimental autoimmune encephalomyelitis (EAE) induced with either whole myelin or the 89-101 peptide itself (Anderton and Wraith (1998) Eur. J. Immunol. 28:1251).

MBP 89-101 Comprises Three T Cell Epitopes

In order to investigate T cell reactivity to the 81-111 region of MBP, lymph node cells from mice primed with 81-111 are stimulated with 81-111 in vitro and these cells are tested with a panel of overlapping 10-mer peptides with two residue shifts covering the 81-111 region (namely: 81-90, 83-92, 85-94, 87-96, 89-98, 91-100, 93-102, 95-104, 97-106, 99-108 and 101-111). The response pattern to peptides covering the 89-101 show stimulatory capacity for 5 adjacent peptides (N terminal 87-96 through to 95-104) reflecting the presence of at least two (and perhaps three) distinct epitopes.

Figure 14:
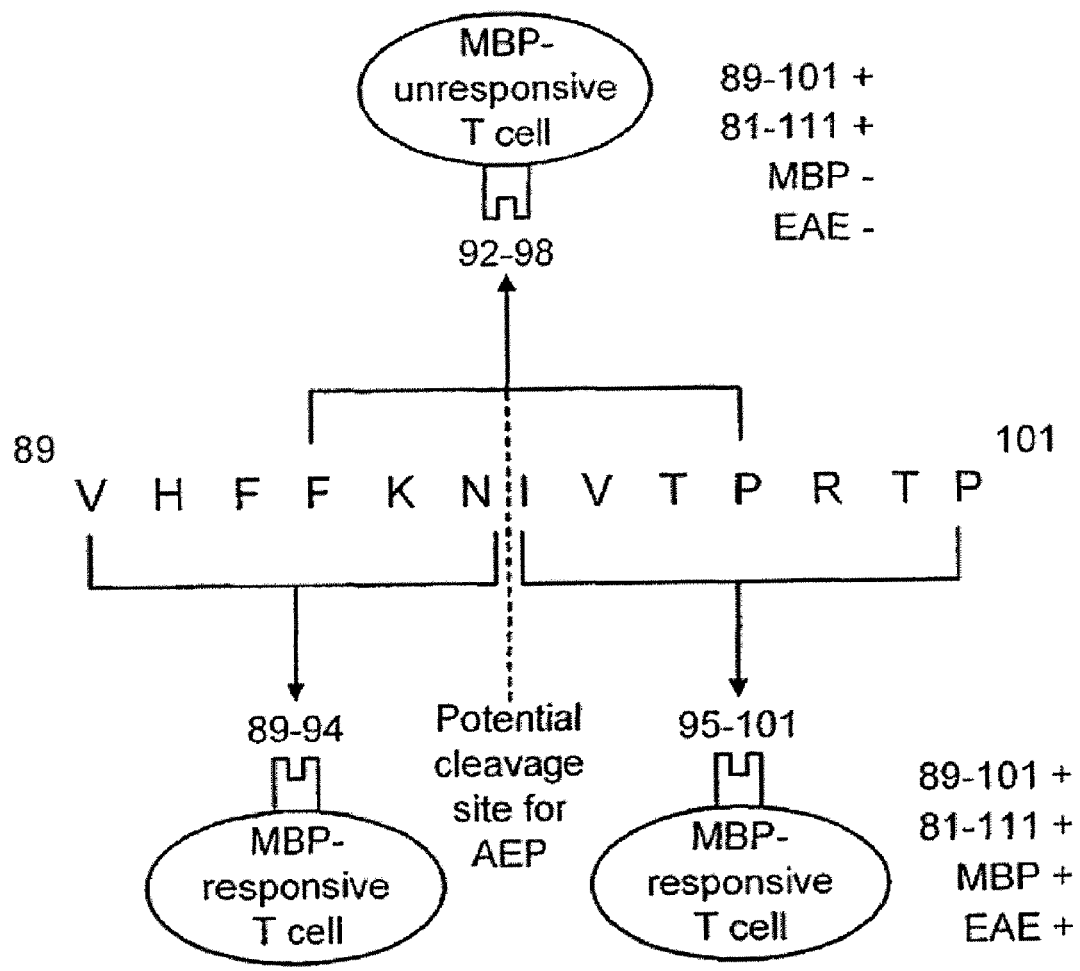
FIG. 14 is an illustration of T cell epitope recognition within the MBP 89-101 sequence. There are three distinct but overlapping T cell epitopes within the sequence: 89-94, 92-98 and 95-101. The potential for cleavage between residues 94 and 95 by the action of asparginyl endoepetidase (AEP) is shown.

In order to investigate this region further, three sub-lines are generated from the original 81-111-responsive T-cell line and these are retested with a panel of overlapping 10-mer peptides with one residue shift covering the 84-106 region. The results reveal the existence of three distinct but overlapping T cell epitopes within the 89-101 sequence: 89-94, 92-98 and 95-101 (see FIG. 14).

MBP Peptide 92-98 is a Cryptic Epitope

The three epitope-specific T cell lines (TCL) show interesting differences when tested to reactivity to the 89-101 peptide and whole recombinant MBP. All three TCL respond to the peptide (89-101) but only the 89-94 and 95-101-specific TCL respond to whole MBP. This indicates that antigen processing of intact MBP preferentially generates ligands for T cells recognising 89-94 and 95-101 but not those recognising 92-98. This suggests that the 92-98 epitope is cryptic (i.e. cannot be generated by processing of native antigen). It seems that the MBP 89-101 peptide can partake in three distinct interactions with the MHC molecule resulting in peptide/MHC ligands which are recognised by three separate T cell populations. Processing of MBP however only generates ligands for two of these T cell populations (see FIG. 14).

Induction of EAE requires T cell recognition of autoantigenic epitopes expressed in the CNS as a result of degradation of intact MBP. Immunisation of mice with peptides comprising only one of the three previously identified T cell epitopes shows that only those containing a naturally processed epitope (89-94 or 95-101) are capable of inducing EAE. This further supports the finding that 92-98 is a cryptic epitope.

MBP Peptide 92-98 is the Dominant Epitope for MBP Region 89-101

As mentioned above, the region 89-101 contains three distinct but overlapping peptides. Of these, peptide 92-98 appears to be dominant for this region. For example, when T cell clones are generated from mice primed with the 89-101 peptide, all six clones which were generated respond to the 92-98. Using 89-101 analog peptides containing individual alanine substitutions at each position, it has been found that substitution of any of the positions 92-98 leads to a lack of responsiveness, showing that alteration of any residues within the 92-98 core has gross effects on recognition of this epitope.

MBP Peptide 89-101 Fails to Tolerize EAE-Relevant T Cells Recognising a Naturally Processed MBP Epitope.

To summaries the findings above, the present inventors have found that a) the 89-101 sequence has the potential to generate 3 distinct T cell epitopes; b) only two of these epitopes (89-94 and 95-101) are generated by antigen processing of intact MBP (both in vitro and in vivo); c) only peptides containing the naturally processed epitopes and not those containing a cryptic epitope are effective at inducing EAE; d) the 89-101 peptide fails to protect against EAE in peptide therapy experiments.

This information provides a basis for investigating the hypothesis that peptide 89-101 fails to tolerize against EAE through a failure to directly ligate the disease relevant T cells. In order to support the hypothesis, the peptide (89-101) should fail to induce tolerance to the major encephalitogenic epitope (89-94) since it will not bind directly to the MHC restriction element (1-$A^s$) in the appropriate conformation. In other words, 89-101 will not act as an APITOPE for T cells responding to 89-94.

Figure 15A:
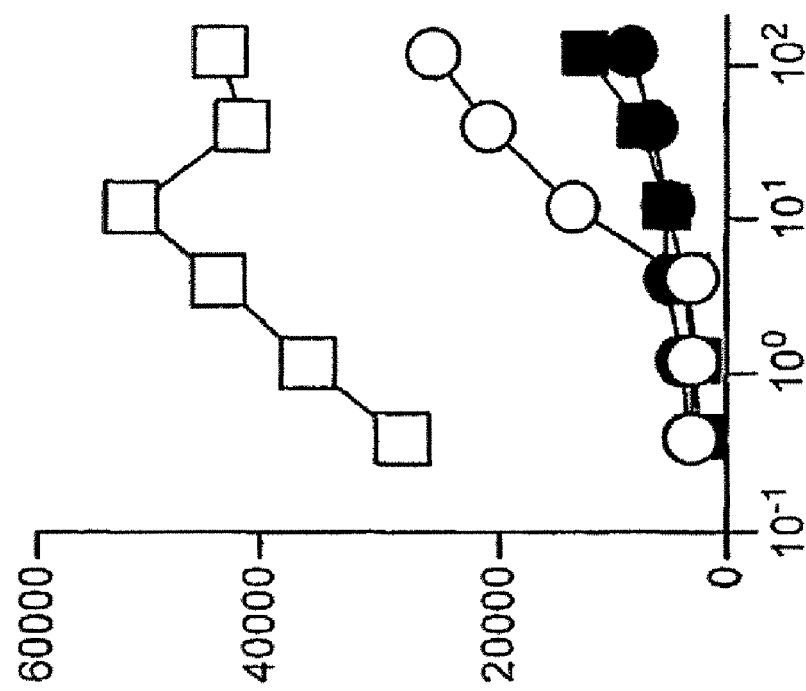
FIG. 15 shows the capacity of MBP peptides 87-96 (A) and 89-101 (B) to act as an APITOPE for T cells responding to the 89-94 epitope.

In order to test this possibility tolerance experiments are performed with the 89-101 and 87-96 peptides (FIGS. 15a and b). The 87-96 peptide contains the epitope (89-94) most effective at inducing EAE.

Methods

Mice received 200 μg of peptide in PBS or PBS alone intraperitoneally on days −8, −6 and −4 prior to 100 μg of peptide in complete Freunds adjuvant on day 0. After 10 days, draining lymph node cells ($6 \times 10^5$ per well) were cultured in X-Vivo 15 medium supplemented with $5 \times 10^{-5}$M 2-mercaptoethanol and 2M L-glutamine with or without antigen for 72 hours. Cultures were pulsed for the final 16 hours with 0.5 μCi $^3$H.thymidine and incorporation measured using a liquid scintillation counter. Results are expressed as means counts per minute for triplicate cultures.

Results

Figure 15B:
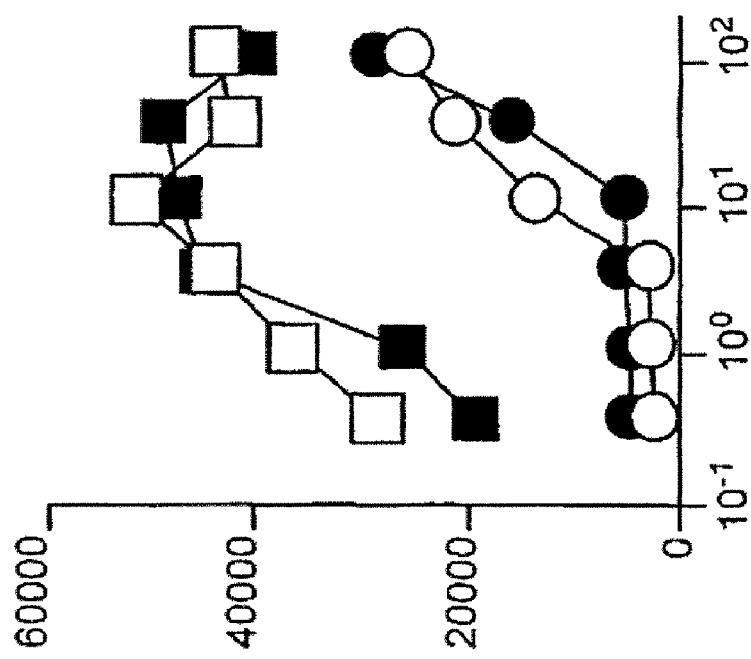

Priming with 87-96 induced a strong recall response to itself and a weaker response to 89-101 (FIGS. 15a and b; □ and ○ respectively). This is consistent with the need for antigen processing to generate 89-94 from 89-101. The use of 87-96 as a tolerogen prior to priming with 87-96 suppressed recall responses to both 87-96 and 89-101 (FIG. 15a a ■ and ●). This fits with 89-94 reactive T cells, once rendered unresponsive in vivo, failing to respond in vitro to 89-94 whether they are generated from 89-96 or 89-101. Crucially, however, the use of 89-101 as the tolerogen prior to priming with 87-96 failed to inhibit recall responses to either 87-96 or 89-101 (FIG. 15b ■ and ●). These data demonstrate that administration of peptide 89-101 in tolerogenic form fails to tolerize to the naturally processed encephalitogenic epitope based on the 89-94 sequence: the 89-101 peptide fails to behave as an APITOPE for the 89-94 epitope.

Without wishing to be bound by theory, the present inventors believe that the observations can be explained by the position of peptide 89-101 in the MHC peptide binding site. If the peptide preferentially binds so that the region 92-98 is in the peptide-binding pocket, then it will be recognised by MBP92-98-specific T cells. This would explain why, when mice are primed with the MBP89-101 peptide, all the T cell clones generated recognize the MBP92-98 epitope. Equally, when 89-101 is used to tolerize T cells, it will mainly tolerize cells which recognize the MBP92-98 epitope. If MBP92-98 is a cryptic epitope, it is not generated by natural processing of the whole antigen and T-cells recognizing this epitope will probably not exist in vivo. Even if an MBP92-98-specific T cells cell did exist in vivo, it would not be relevant to the disease. Hence, 89-101 fails to prevent EAE induced with whole MBP.

Example 3

Peptide Therapy for a Mouse Model of MS

The present inventors have previously shown that a single dose of peptide antigen administered systemically either by the intraperitoneal (Liu and Wraith (1995) Int Immunol 8:1255-1263) or intranasal (Metzler and Wraith (1993) 5:1159-1165) route will effectively protect mice from experimental autoimmune encephalomyelitis (EAE) for up to three months (Metzler and Wraith (1999) Immunology 97:257-263). At least 5 doses of peptide were required to induce tolerance in the Tg4-transgenic mouse (Burkhart et al (1999) 11:1625-1634) expressing an EAE-specific T cell receptor (Liu et al (1995) Immunity 3:407-415). Recent work has shown the intranasal (IN) route is safer than the intraperitoneal (IP) route in the Tg4 mouse, even though both approaches are equally safe in the non transgenic mouse.

Peptide 83-99 of MBP is tested in the Fug/D6 transgenic mouse which expresses both the appropriate HLA-DR2 class II MHC molecule and a TCR from a human T cell clone specific for this peptide. Mice are treated with peptide following either the standard dose used for treatment of the Tg4 transgenic mouse (Tg4 protocol) or the desensitisation protocol of peptide dose escalation which has been used in treatment of patients suffering from allergy (Desensitisation protocol).

Tg4 protocol: Groups of mice are treated by intranasal administration of peptide 83-99 (4 mg/ml in phosphate-buffered saline (PBS)) or PBS alone in a total volume of 25 µl. Mice are treated every $1^{st}$ and $5^{th}$ day of the week for 5 weeks giving a total of 10 doses. At the beginning of week 6 each mouse is injected with peptide 83-99 in Complete Freunds Adjuvant (CFA) and also receives an IP injection of Pertussis Toxin (200 ng) on day 1 and 3. The progression of EAE is monitored for at least 30 days.

Desensitisation protocol: Groups of mice are treated by intranasal administration of an escalating dose of peptide 83-99 or PBS alone in a total volume of 25 µl. The dose escalation starts at 0.1 µg and proceed through 1, 3, 6, 12, 50 and then three times 100 µg. Mice are treated every $1^{st}$ and $5^{th}$ day of the week for 5 weeks giving a total of 10 doses. At the beginning of week 6 each mouse is injected with peptide 83-99 in Complete Freunds Adjuvant (CFA) and also receives an IP injection of Pertussis Toxin (200 ng) on day 1 and 3. The progression of EAE is monitored for at least 30 days.

Example 4

Nasal Administration of an APITOPE Cocktail to MS Patients

A vaccine is made comprising the MBP peptides 30-44, 83-99, 110-124 and 130-144 (i.e. some of those epitopes of MBP which have been identified as APITOPEs). The vaccine is given to thirty-five patients in a Phase Ia/Ib trial. The trial is a single crossover trial in which patients remain untreated for three months followed by a single dose of peptide (Ia). Patients are then monitored for three months following the single dose of vaccine to assess safety. Treatment then consists of twice weekly administration by intranasal deposition. For each patient: clinical activity is analysed monthly by magnetic resonance imaging; immunological activity is monitored using a kinetic response assay for proliferation; and cytokine production is monitored using a cell-based ELISA.

The trial initially involves treatment of 5 patients suffering from chronic progressive (CP) disease. These patients are selected on the basis of low MRI activity and are treated first with the highest dose of peptides. Treatment is started in the CP patient group because they are most likely to demonstrate any possible harmful effects as evidenced by an increase in MRI activity. Treatment of relapsing remitting patients begins once it is clear that the both single and multiple dose treatment is safe in the CP group. A larger group of 30 relapsing remitting patients are recruited on the basis of their suffering enhancing MRI lesions during a monitoring period of 3 months. These are divided into three groups to be treated with a high, medium or low dose of peptide.

| TIME POINT (MONTHS) | CHRONIC PROGRESSIVE (CP) PATIENTS | RELAPSING REMITTING (RR) PATIENTS |
| --- | --- | --- |
| 0 | Begin monthly monitoring | |
| 3 | Start phase Ia (single dose of peptide) with MRI at 1-2 weeks after treatment and monthly monitoring | |
| 6 | Start phase Ib (twice weekly dose of peptide) and continue monthly monitoring | Begin monthly monitoring and recruit patients with enhancing lesions |
| 9 | | Start phase Ib (twice weekly dose of peptide) and continue monthly monitoring |
| 12 | End treatment and continue monthly monitoring for further 6 months | |
| 15 | | End treatment and continue monthly monitoring for further 6 months |

Abbreviations: APC=antigen presenting cells; MHC=major histocompatability complex; TCR=T cell receptor; EAE=experimental autoimmune encephalomyelitis; APITOPE=antigen processing independent epitope; APIPS=antigen processing independent presentation system; a.a.=amino acid; MS=Multiple Sclerosis; MBP=myelin basic protein; PLP=proteolipid protein; TCL=T cell line; TCC=T cell clone; PBMC=peripheral blood mononuclear cells; PPD=*Mycobacterium tuberculosis* purified protein derivative; PHA=phytohemagglutinin.

Example 5

Identification of HLA-DQ6 Restricted Myelin Basic Protein T-Cell Epitopes

MHC Class II genes confer susceptibility to multiple sclerosis (Nepom and Ehrlich (1991) Ann. Rev. Immunol. 9: 493-525). Within Caucasians in Northern and Central Europe, Australia and Northern America the association is linked to the MHC molecule HLA-DR2 (DR2a [DRB5*0101] and DR2b [DRB1*1501], Haines et al (1998) Human Mol. Genet. 7: 1229-1234). Although the DR2 and DQ6 alleles of MHC are found at different loci, there is significant linkage disequilibrium between the two alleles. The concordance between the two alleles is 99%, much greater than expected if the alleles were randomly re-associated. Therefore the possibility arises that certain T-cell epitopes associated with MS may be HLA-DQ6 restricted rather than HLA-DR2 restricted.

The aim of this study was to identify whether human MBP T-cell epitopes are presented by the HLA-DQ6 molecule to T-cell clones isolated from HLA-DR2 positive MS patients. T-cell activation was measured by T-cell proliferation using [$^3$H]-Thymidine incorporation.

Materials and Methods
Peptide Antigens

MBP peptides 30-44, 130-144 and 139-153 were synthesized using L-amino acids and standard F-moc chemistry on an Abimed AMS 422 multiple peptide synthesiser.

Antigen Presenting Cells

L-cells transfected with either HLA-DQ6, HLA-DR2a or HLA-DR2b, or Mgar cells (EACC, Porton Down, UK) which express HLA-DQ, DP and DR were used as APCs.

T-cell Clones

T-cell clones MS 49:D3 and MS17:A2 were generated from MS patients and clone N5:19 was generated from a normal individual. All three clones were DR2 positive.

Antigen Presentation Assay

Antigen presenting cells were incubated with the various concentrations of peptide and the appropriate T-cells. Proliferation, and therefore activation, of the T-cells was measured by [$^3$H]-Thymidine incorporation, and expressed as the stimulation index (SI=corrected counts per minute (ccpm) culture containing peptide/ccpm culture without peptide).

Results

Figure 16:
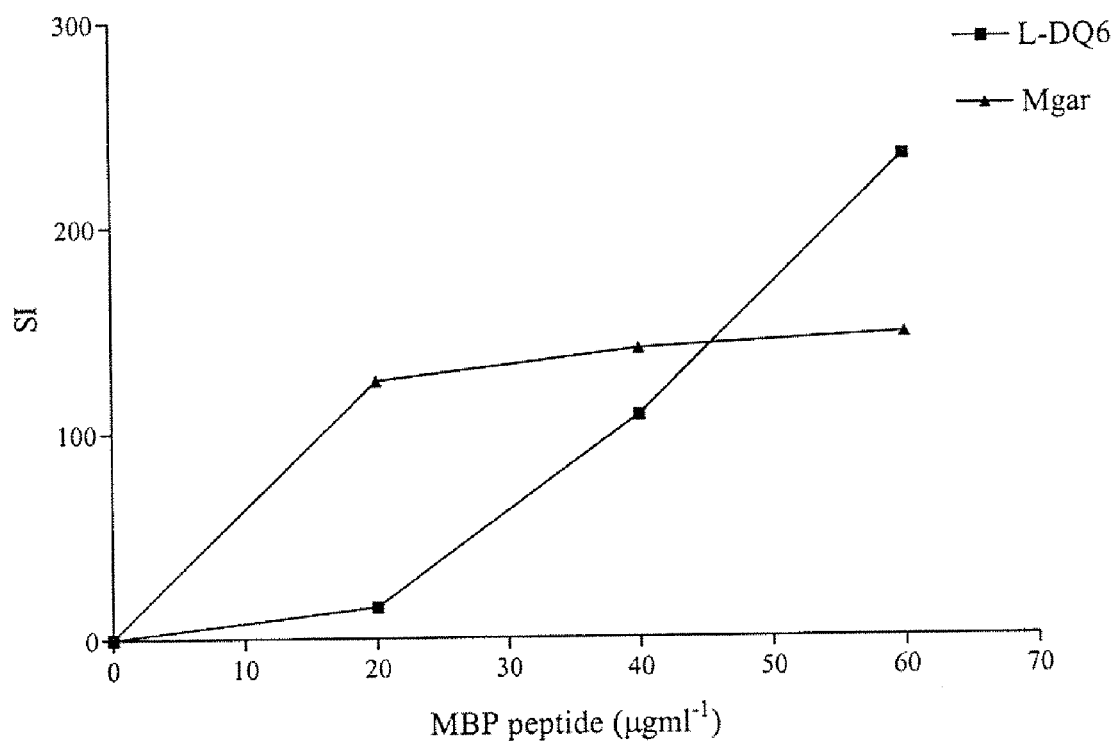
FIG. 16 shows the presentation of MBP 30-44 by HLA-DQ6 to T-cell clone MS49:D3.
Figure 17:
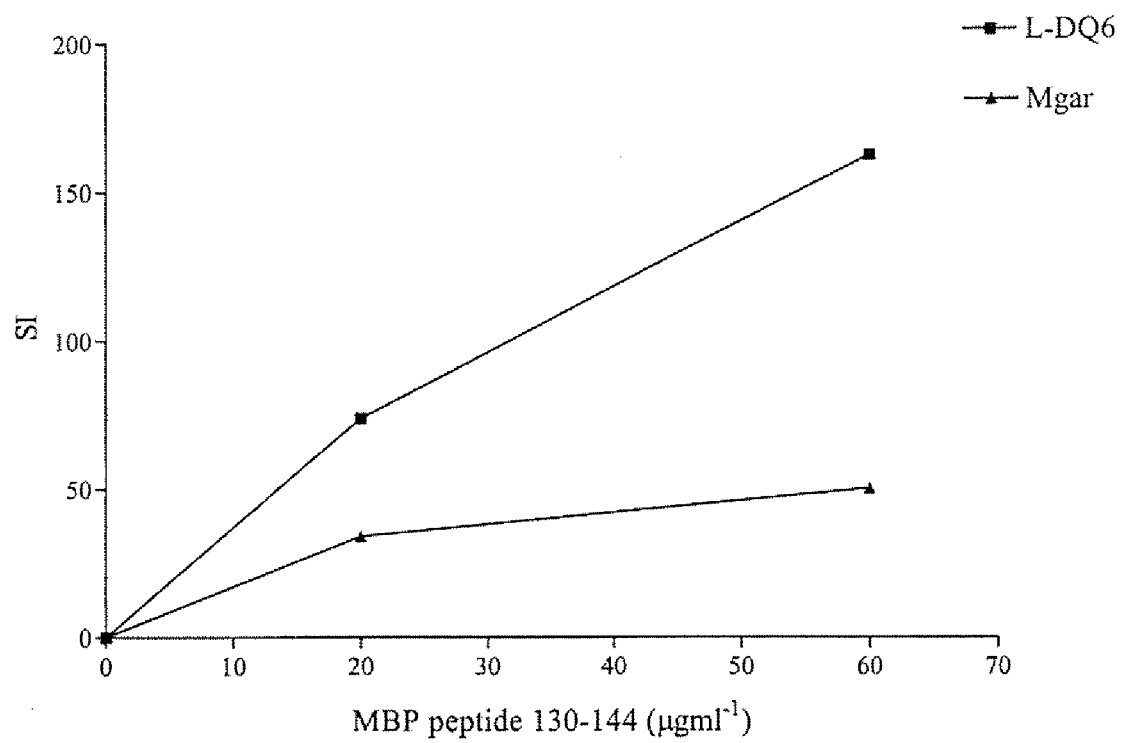
FIG. 17 shows the presentation of MBP 130-144 by HLA-DQ6 to T-cell clone MS 17:A2.

When peptide MBP 30-44 was presented by L cells transfected with HLA-DQ6, T-cell clone MS 49:D3 gave a very strong proliferative response (1.5 fold greater than to Mgar control cells) at the highest peptide concentration (FIG. 16). When MBP 130-144 was presented by L cells transfected with HLA-DQ6 an even stronger response was induced in MS17:A2 T-cells (3.24 fold increase in proliferation compared to Mgar control cells—FIG. 17).

Figure 18:
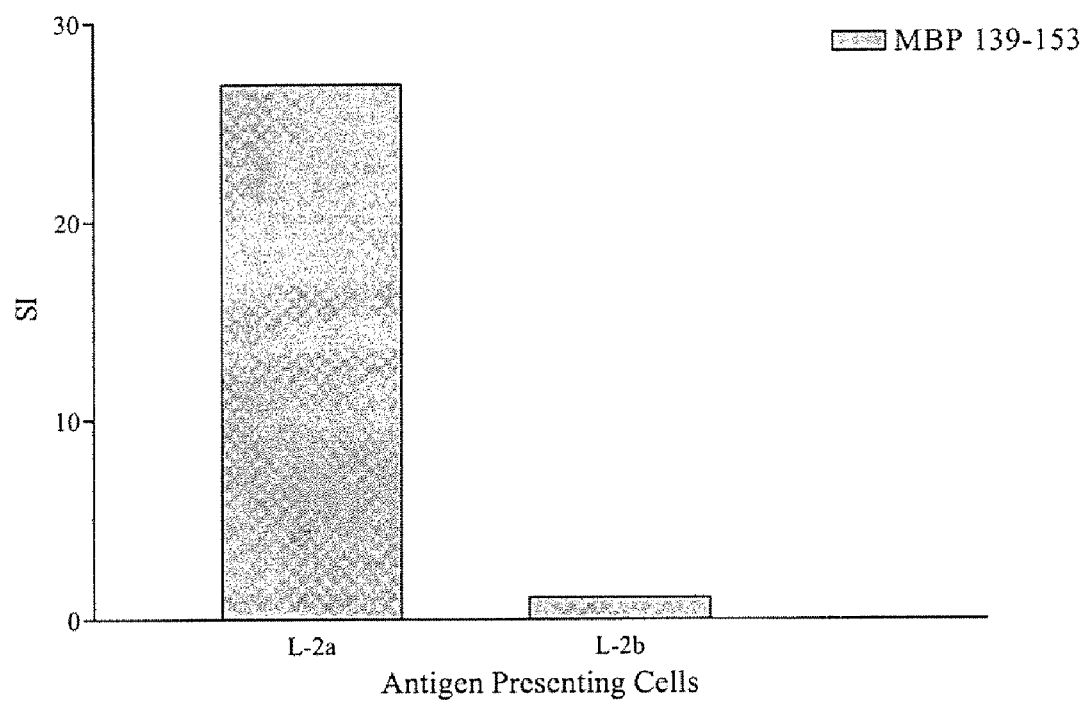
FIG. 18 shows the presentation of MBP 139-153 by HLA-DR2a and HLA-DR2b transfected L-cells to T-cell clone N5:19.

A third T-cell clone isolated from a DR2 individual N5:19 responded to the major epitope MBP 140-154 and to a series of overlapping 15mer peptides spanning this region (138-156). Peptide 139-153 stimulated proliferation of the N5:19 T-cell clone when presented by HLA-DR2a transfected L-cells, but not HLA-DR2b transfected L-cells (FIG. 18).

Conclusion

T-cell clones isolated from HLA-DR2 positive individuals respond to HLA-DQ6 restricted MBP T-cell epitopes. This implies that the association of HLA-DR2 with multiple sclerosis is not confined to DR2 restriction of MBP T-cell epitopes but may also be DQ6 restricted.

In the MBP composition of the present invention, two of the peptides are HLA-DQ6 binding (MBP 30-44 and 131-145) and two are HLA-DR2 binding (MBP 140-154 and 83-99). Therefore, peptide therapy with these APITOPEs may be directed to either HLA-DR2 or HLA-DQ6 individuals.

Example 6

Induction of Tolerance with APITOPE MS6 in a HLA:DR2 Transgenic Mouse

This study was designed to demonstrate that an APITOPE (APITOPE MS6), when presented by an MHC Class II molecule, can induce immunological tolerance in a humanized mouse model of multiple sclerosis. APITOPE MS6 is an APITOPE selected from within T-cell epitopes of MBP corresponding to MBP 140-154, and is presented by MHC Class II on antigen presenting cells, and can stimulate T-cells without being processed (see WO 03/064464). The mouse model used was transgenic for the human MHC molecule HLA:DR2 (DRB1*1501) (Madsen et al(1999) Nature Genetics 23:343-347).

The induction of anergy or changes in the CD4+ T-cell population in a mouse after administration of an APITOPE may be monitored by a reduction in T-cell proliferation when challenged with the antigen in vivo.

Materials and Methods
Peptide Synthesis

APITOPE MS6 (MBP peptide 140-154) was synthesised using L-amino acids and standard F-moc chemistry on an Abimed AMS 422 multiple peptide synthesiser.

Mice and Tolerance Induction

HLA:DR2 transgenic mice aged 8-12 weeks were used in the study. The mice were tolerized by pre-treatment with 100 μg of APITOPE MS6 in 254l of phosphate buffered saline (PBS) or 25 gl PBS alone, by intranasal administration on days −8, −6 and −4 prior to immunisation on day 0.

Following tolerization, mice were immunised subcutaneously with 100 μl of an emulsion containing an equal volume of Complete Freund's Adjuvant (CFA) and PBS containing 200 μg of APITOPE MS6 and 400 μg heat-killed *Mycobacterium tuberculosis*. A control group of mice, previously tolerized with PBS intranasally, were immunised without peptide.

At 10 days post subcutaneous immunisation, draining popliteal and inguinal lymph nodes were removed and T-cell activation was assessed by assaying the proliferation of T-cells in response to various concentrations of APITOPE MS6. Proliferation was measured by [$^3$H]-Thymidine incorporation, and expressed as the stimulation index (SI=corrected counts per minute (ccpm) culture containing peptide/ccpm culture without peptide).

Results

Figure 19:
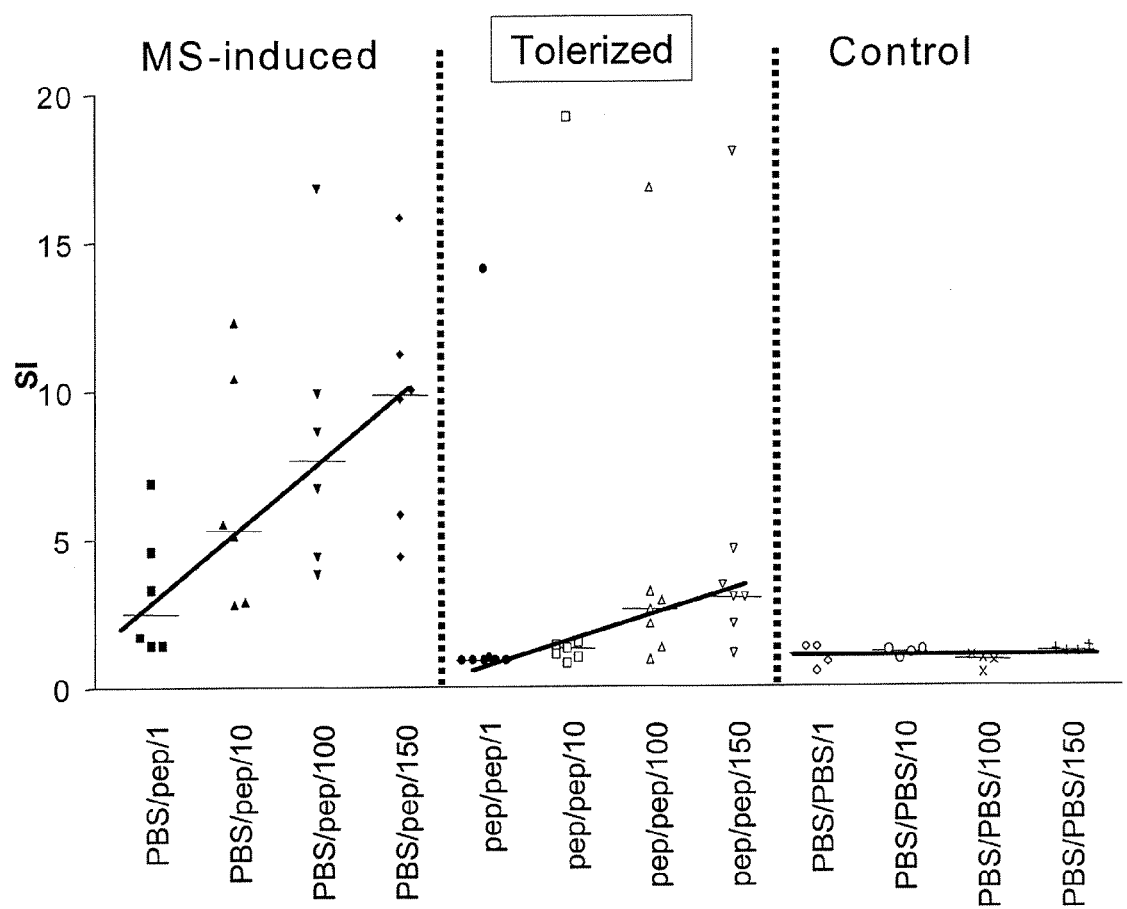
FIG. 19 shows the proliferative response of lymph node cells following tolerization with APITOPE MS6 (MBP 140-154).

Group A mice that were tolerized with PBS and then immunised with APITOPE MS6 responded to antigenic stimulation when re-challenged with APITOPE MS6 in a dose dependent manner (FIG. 19). With increasing concentration of peptide the SI increased from a median of 2.5 to 10. All the mice in this group demonstrated that PBS administered intranasally could not induce tolerance to APITOPE MS6.

In contrast, intranasal pre-treatment with APITOPE MS6 had a profound effect on the proliferative response of lymphocytes stimulated with this peptide. Lymphocytes from Group B mice were unable to respond to any significant degree, even at the high peptide concentration of 150 μg/ml (SI median 3, FIG. 19). These data suggest that APITOPE MS6 has induced tolerance in lymphocytes from HLA-DR2 mice.

Lymphocytes extracted from mice which had been pretreated and immunised with PBS (Group C) failed to show any response to APITOPE MS6 (FIG. 19). This lack of response to the peptide within Group C confirms that the proliferative response seen in Group A was indeed a response to immunisation with APITOPE MS6.

Conclusion

These data support the hypothesis that an MBP peptide (APITOPE MS6) that does not require processing and binds to HLA:DR2 MHC Class II molecules, can induce tolerance when administered intranasally.

Example 7

Induction of Tolerance with APITOPE MS7 (MBP 83-99) in HLA:DR2 and T-cell Receptor (MBP) 82-100 Double-Transgenic Mice This study investigates the ability of APITOPE MS7 (MBP peptide 83-99) to induce tolerance in double transgenic mice expressing HLA:DR2 together with the T-cell receptor for the HLA: DR2 bound myelin basic protein (MBP) 82-100 peptide.

Splenocytes from these double transgenic animals proliferate in vitro in response to APITOPE MS7. Reduction or abrogation of the in vitro splenocyte response to an APITOPE following its repeated administration in vivo indicates that a state of tolerance has been achieved.

Tolerance induction has been attempted using both the intranasal and subcutaneous/intradermal routes of APITOPE administration.

Materials and Methods
Tolerance Induction

Groups of 6 or 7 age (8-12 weeks) and sex matched double transgenic mice were used. In the first experiment one group was treated ten times intranasally with 100 µg APITOPE MS7 in 25 µl PBS at regular intervals over a period of three weeks. The control group received PBS alone. In the second experiment the same amount of peptide was given by subcutaneous/intradermal administration in 100 µl of PBS. The control group received the same volume of PBS.

Proliferation Assay

Three days after the last administration of peptide or PBS, the spleens were harvested and cell suspensions prepared. The splenocytes were incubation with 0.5 or 5 µg/ml APITOPE MS7, and assessed for proliferation by [$^3$H]-Thymidine incorporation after 48, 72 and 96 hours of culture. Results are expressed as stimulation indices (SI=counts per minute (cpm) of culture containing antigen/counts per minute without antigen).

Cytokine Measurement

In the second experiment, where tolerance induction was induced via the subcutaneous/intradermal route, cell culture supernatants from the splenocytes were collected at 48 and 72 hrs of culture, and assayed for the presence of IFN-γ and interleukin-2 (IL-2) using an enzyme linked immunosorbant assay (ELISA).

Results

Figure 20:
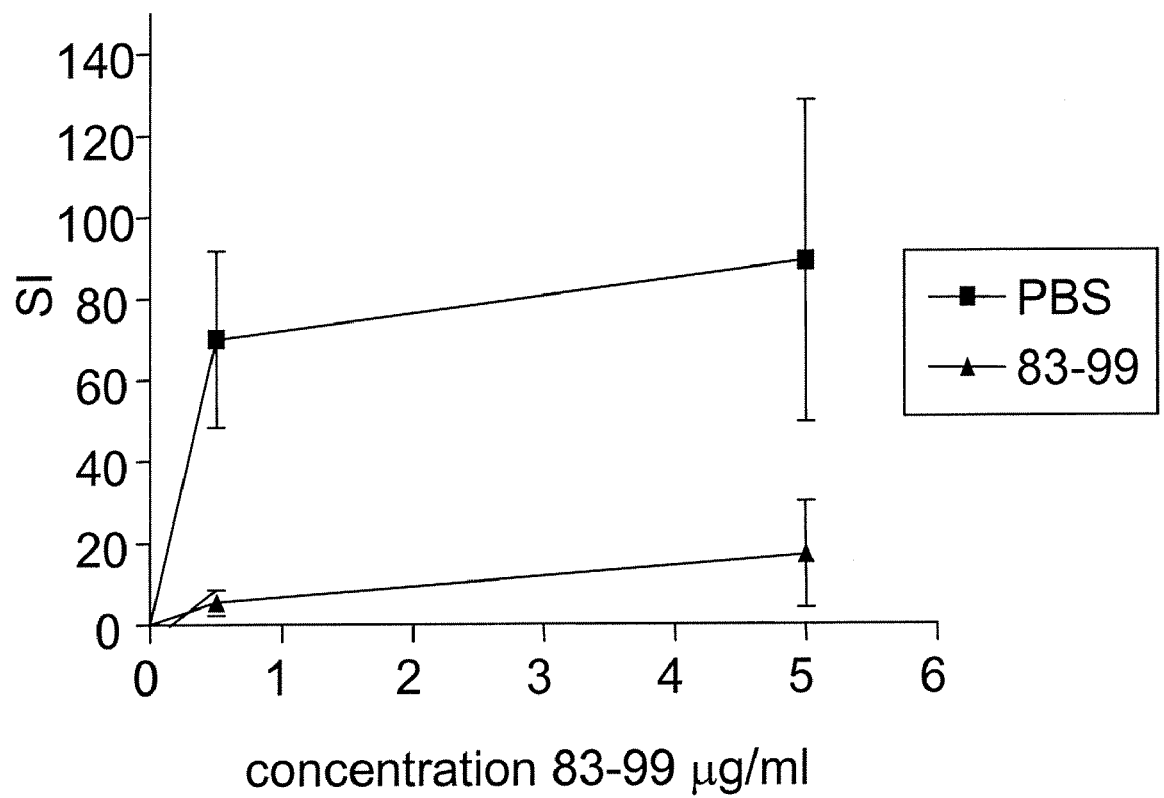
FIG. 20 shows the proliferation of splenocytes in response to MBP 83-99 (APITOPE MS7). Splenocytes were obtained from mice treated by intranasal administration of either PBS or MBP 83-99.
Figure 21:
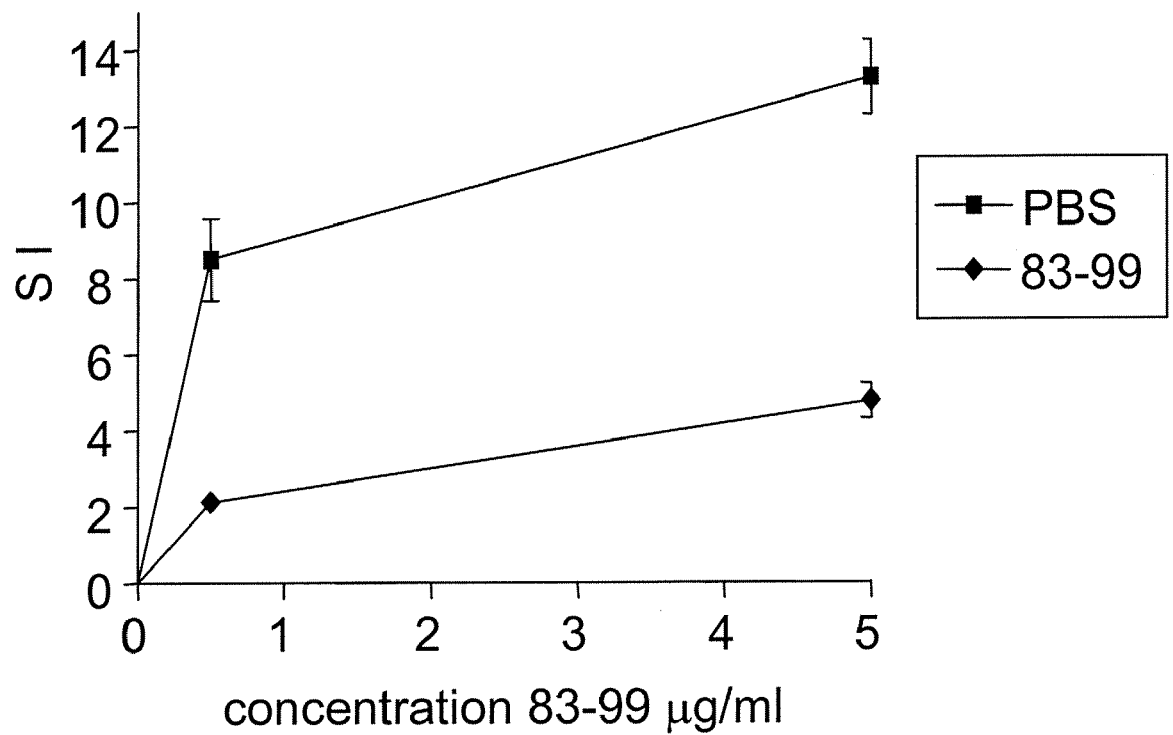
FIG. 21 shows the proliferation of splenocytes in response to APITOPE MS7 (MBP 83-99). Splenocytes were obtained from mice treated by subcutaneous/intradermal administration of either PBS or APITOPE MS7 (83-99).

At all three time points investigated, an increase in proliferation was observed in splenocytes from mice treated with PBS, via both the intranasal and subcutaneous route, in response to MBP 83-99, the magnitude of the response increasing with peptide concentration. A striking reduction in proliferation was observed in splenocyte cultures from mice treated with MBP 83-99 by both routes of administration. As shown in FIG. 20, after 72 hrs the mean SI observed with cultures containing 5 µg/ml 83-99 was 17 in mice treated intranasally with MBP 83-99. In the corresponding cultures from control mice treated with PBS, a mean SI of 89 was observed. Similarly, as shown in FIG. 21, administration of APITOPE MS7 (MBP 83-99) subcutaneously resulted in a decrease in mean SI from 124 in the PBS treated animals to 49 in animals treated with APITOPE MS7 (83-99).

Figure 22A:
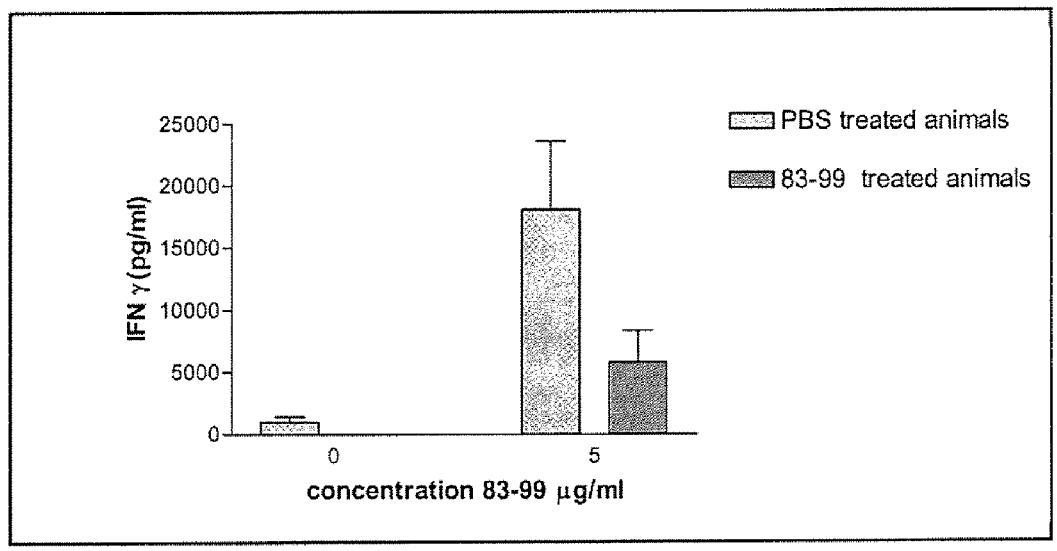
FIG. 22A shows the production of IFNγ by splenocytes obtained from mice treated by subcutaneous/intradermal administration of either PBS or MBP 83-99.
Figure 22B:
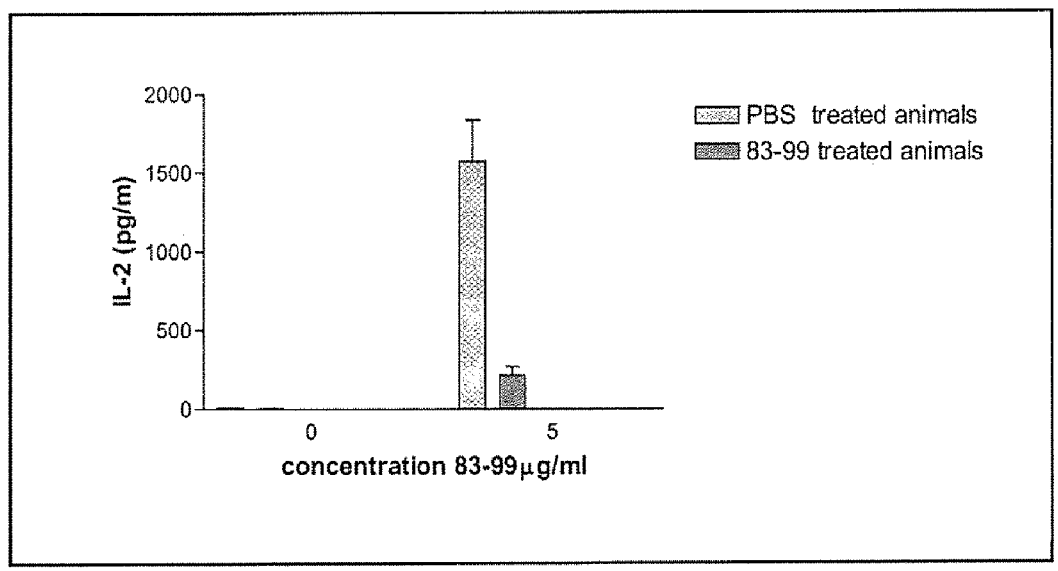
FIG. 22B shows the production of IL-2 by splenocytes obtained from mice treated by subcutaneous/intradermal administration of either PBS or MBP 83-99.

The levels of IFNγ and IL-2, detected in culture supernatants from 48 hr cultures, are shown in FIGS. 22a and 22b, respectively. The repeated treatment with peptide in vivo is seen to bring about an impressive reduction in secretion of both cytokines, paralleling the reduction in the proliferative response.

Conclusion

These results indicate that tolerance to APITQPE MS7 can be successfully induced in a mouse model designed to mimic the human system and supports its potential for use in multiple sclerosis therapy. Furthermore its efficacy is retained when administered by the subcutaneous/intradermal route, the route of choice for humans.

Although the in vivo efficacy of APITOPEs MS6 and MS7 has been demonstrated it is not at present possible to demonstrate the efficacy of APITOPEs MS1 and MS4. This is because of the lack of transgenic mice expressing the HLA-DQ6 molecule. Mice expressing the molecule have been created, but it has been found that they fail to generate CD4 T-cells in the thymus and do not therefore mount an immune response to antigen in the context of HLA-DQ6.

Example 8

Dose Escalation Study with a Composition of Four MBP Peptides

The combination of four peptides (MBP 30-44, 131-145, 140-154 and 83-99) was used in an open-label, dose-escalation study of ATX-MS-1467 in patients with secondary progressive multiple sclerosis.

Patients were monitored at four weeks and three months after the final study dose for visual acuity (i.e. reduction in optic neuritis), immunological parameters and inflammation in the CNS.

Materials and Methods
Formulations and Dosages

Each of the four peptides is manufactured independently under contract using solid phase peptide synthesis, and purified using HPLC. They are stored lyophilised.

ATX-MS-1467 is a 1:1:1:1 mixture of APITOPEs MS1, MS4, MS6 and MS7 in phosphate buffered saline for intradermal administration.

Two strengths of ATX-MS-1467, designated ATX-MS-1467A and ATX-MS-1467B containing 4 mg/ml and 0.5 mg/ml of peptide, respectively were prepared to allow dose escalation. The regime employs five dose-escalating injections (25, 50, 100, 400 and 800 µg total dose) given 7 to 14 days apart. The patients then receive a second 800 µg dose 7 to 14 days following the first 800 µg dose.

After receiving all six doses of study medication, the patient is assessed at four-weeks and at 3 months after the final study dose.

Visual Acuity Test

A standard size Snellens chart for testing at 6 metres is used, with back light illumination and patient sitting at 6 metres distance (FIG. 23).

Each eye is examined separately for the lowest line on the chart that the patient is able to read. This is then denoted as Visual acuity=6/(the line which the patient has read).

Immunoassays i) T-Cell Proliferation:

Cryopreserved PBMC are set up in 1 ml cultures containing $1.5 \times 10^6$ cells in A-MEM in 48 well tissue culture plates (Nunc International, Costar, Corning Inc. New York USA). Responses to MBP and peptide antigens at various concentrations are monitored over a period of 10 days. Control wells contain no antigen. After 20 hrs or 2, 4, 6, 8 and 10 days of culture, duplicate 100 µl aliquots of cell suspension are removed from each 1 ml culture to measure proliferation in response to antigen by uptake of [3H] thymidine.

ii) Measurement of Secreted Cytokines (IL-2 and IL-4, IL-5, IL-10, TNF-α and IFN): Cytometric Bead Array Assay;

Culture supernatant cytokine levels are determined using the Cytometric Bead Assay (Becton Dickenson Biosciences, Cowley, Oxford, UK) following the manufacturer's instructions. Following acquisition of sample data using the FACS Calibur (BD Biosciences), results are generated in graphical and tabular form using BD CBA software. The minimum quantifiable levels of cytokine are as follows: IL-2 and IL-4 2.6 pgml-1, IL-5 2.4 pgml-1, IL-10 and TNF-α2.8 pgml-1, IFN-γ 7.1 pgml-1.

Quantitative Real Time PCR to Measure RNA of Cytokines (IL-2, IL-10 IFN-γ and TNF-α)

For analysis of IL-2, IL-10, IFN-γ and TNF-α, PCR reactions are carried out in a final volume of 20 µl containing cDNA, PCR buffer, 6.25 mM $MgCl_2$, 0.4 mM dNTP mix, forward and reverse primers (forward primer concentrations: IL-2 300 nM, IL-10 600 nM, IFN-γ 600 nM, TNF-α 600 nM, reverse primer concentrations: IL-2 600 nM, IL-10 900 nM IFN-γ 900 nM, TNF-α 600 nM), 200 nM FAM-TAMRA probe and 0.05 µl–1 Platinum Taq polymerase (Invitrogen). The cycling conditions are as follows: an initial denaturation step at 94° C. for 30s, followed by 35 cycles with 15s at 94° C. and 1 min at 60° C. For P-2 microglobulin, the PCR mix described above is supplemented with 0.1 µM forward and reverse primers, 3 mM $MgCl_2$ and quantitated with SYBR Green I (Molecular Probes Inc., X30000 dilution of stock). Following a 1 min denaturation step at 95° C., amplification continues with 35 cycles of 15s at 94° C., 1 min at 61° C. and 1 min at 72° C. The PCR reactions and fluorescence detection of amplicons generated is performed on an Opticon 2 system (MJ Research, USA). Baseline fluorescence is established by taking measurements from cycle 1 to 10. Ct values are calculated by determining the point at which the fluorescence exceeds 8-10 times the standard deviation of the baseline. Samples are assayed in duplicate and copy number calculated from a standard curve for each target DNA. Differences in RNA input copy number and cDNA synthesis are corrected by normalizing cytokine expression to the expression of P-2 microglobulin.

HLA Typing

Analysis of HLA gene expression is performed by a standard single-strand conformation polymorphism, polymerase chain reaction technique on DNA extracted from peripheral blood leukocytes. The HLA-type of each patient is used for interpretation of the results of immunological assays.

Serum Anti-Peptide Antibody Assays 96 well plates are coated with 1-10 µg/ml of each APITOPE MS1, MS4, MS6 or MS7 at pH 9.6 overnight at 4° C. Plates are washed four times with phosphate-buffered saline, pH 7.2, 0.05% Tween (PBS-Tween) and the wells blocked with 5% FCS in PBS for 1 h at room temperature. Sera are diluted 1:100 in PBS-Tween and incubated in duplicate wells for one hour at room temperature. After 4 washes, Goat anti-human IgG-horseradish peroxidase conjugate (Sigma) diluted 1:12 000 in PBS is added to each well and the plates incubated for one hour at room temperature. After 4 washes 0.4 mg/ml of o-phenylenediamine dihydrochloride (Sigma) plus 30% hydrogen peroxide is added and incubated at room temperature for 15-20 min. Colour development is stopped with 2.0 M $H_2SO_4$ (50 µl) and optical density values (ODs) measured at 490 nm with an ELISA plate reader. Results are reported as OD for 1:100 diluted sera.

MRI Scan

Inflammation in the CNS is investigated using a gadolinium-enhanced MRI scan. The volume and number of enhancing lesions is examined and compared with the baseline scan.

Example 8A

Monitoring Visual Acuity

Optic Neuritis (ON) is an inflammation, with accompanying demyelination, of the Optic Nerve serving the retina of the eye. ON is one of the most frequently presenting symptoms of multiple sclerosis, and is the most common symptom at onset of MS. Typical symptoms of ON include: blurring of vision, loss of visual acuity, loss of some or all colour vision, complete or partial blindness and pain behind the eye.

The effect of treatment with ATX-MS-1467 on optic neuritis resulting from the neuroinflammatory process involved in MS was investigated. ATX-MS-1467 was given following the dose-escalation protocol outlined above, and then one month following treatment the patient's visual acuity was tested using a standard Snellens chart (FIG. 23).

The results show a clinically significant improvement in visual acuity one month post treatment. This was demonstrated in analysis of the initial visual acuity examination at screening compared to the one month follow up test. Initial screening sight measurements of 6/24 and 6/6 (in right and left eyes respectively) improved to 6/6 (right eye) and 6/6 (left eye) post treatment. The patient's eyesight had previously been unchanged for the past two years.

Example 8B

Monitoring Immunological Parameters

As explained above, the effect of peptide therapy with a cocktail containing four APITOPE™ peptides from myelin basic protein (ATX-MS-1467) has been investigated on MS patients. Each patient was screened at entry into the trial, up to 14 days prior to the first dose (visit 1). The first dose of 25 µg of ATX-MS-1467 was given on visit 2, 50 µg on visit 3, 100 µg on visit 4, 400 µg on visit 5 and 800 µg on both visits 6 and 7. Further examinations were conducted at one month and three month follow-ups (visits 8 & 9).

Blood samples were collected at visits 1 and visits 3 to 9 and tested for immune responses to various antigens including purified protein derivative (PPD) of *Mycobacterium tuberculosis*, as a positive control, purified human myelin basic protein (MBP) and ATX-MS-1467. The immune responses to be measured include in vitro T-cell proliferation, secretion of cytokines into tissue culture supernatants and generation of cytokine RNA.

Results

Figure 24:
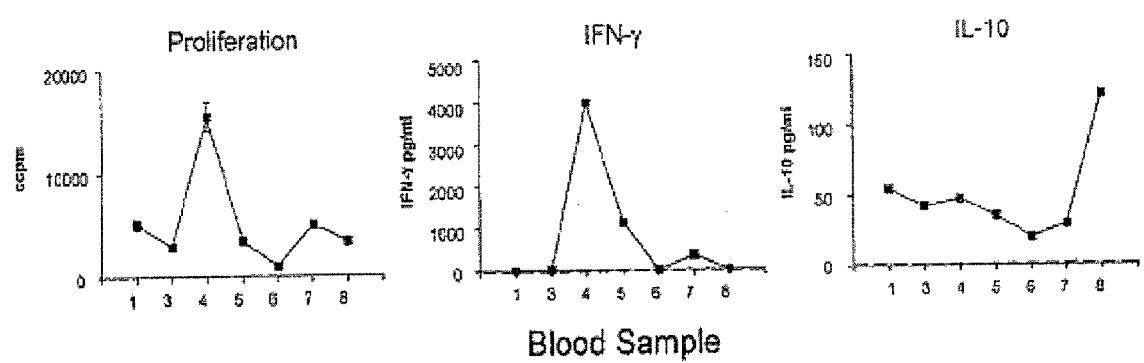
FIG. 24 shows patient PBMC responses to human myelin basic protein (MBP).

A significant response to MBP was seen, with a peak in proliferation at visit 3 (FIG. 24). This correlated with a peak in secretion of interferon gamma. Importantly, however, the level of interferon gamma secretion fell after the third visit and was at background level by visit 8. IL-10 levels did not change significantly until visit 7 at which point there was a significant increase in secretion of this cytokine. Levels of IL-4, IL-5 and TNF alpha were close to background in response to MBP at all time points.

Figure 25:
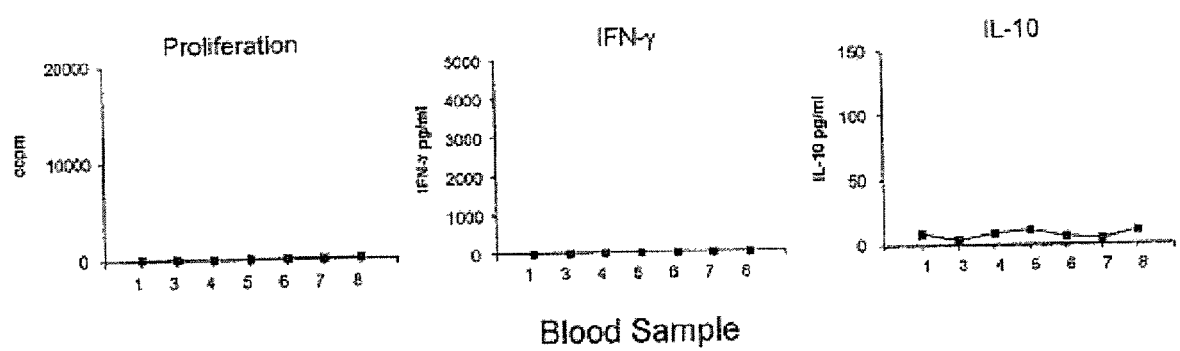
FIG. 25 shows patient PBMC responses to ATX-MS-1467.

No proliferative response or increased cytokine response was observed to ATX-MS-1467 (FIG. 25).

Conclusion

A response to MBP was observed at visit three demonstrating a heightened secretion of IL-2 and interferon gamma, correlating with a peak in proliferation at this time point. This increase in response is thought to be attributable to the administration of peptides.

Importantly, however, the transient increase in cytokine secretion was followed by a return to baseline levels of interferon gamma. There was also a significant increase in IL-10 secretion following the second administration of ATX-MS-1467 at the highest dose. It has previously been reported that, in animal models, specific immunotherapy with synthetic peptides is effective and results in the induction of IL-10 secreting regulatory T cells. The induction of IL-10 secreting regulatory T cells in mice involves a transient response to peptides with secretion of interferon gamma at low levels (Burkhart et al., 1999 Int Immunol 11: 1625-1634; Sundstedt et al., 2003 J Immunol 170:1240-1248). This is followed by a decrease in interferon gamma and a concomitant increase in IL-10. The kinetics of cytokine secretion displayed following treatment with ATX-MS-1467 effectively reproduces the pattern previously observed in experimental mice, suggesting that ATX-MS-1467 may induce IL-10 secreting regulatory T cells.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or biology or related fields are intended to be covered by the present invention. All publications mentioned in the above specification are herein incorporated by reference.

The invention claimed is:

1. A human myelin basic protein (MBP) peptide, wherein said peptide is capable of binding to an MHC class I or II molecule without further antigen processing and being presented to a T-cell, and wherein said peptide is MBP 30-44 (SEQ ID NO: 1).

* * * * *

UNITED STATES PATENT AND TRADEMARK OFFICE
CERTIFICATE OF CORRECTION

Page 1 of 1

PATENT NO. : 8,343,500 B2
APPLICATION NO. : 11/979224
DATED : January 1, 2013
INVENTOR(S) : David Cameron Wraith et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1058 days.

Signed and Sealed this
Eleventh Day of November, 2014

Michelle K. Lee
*Deputy Director of the United States Patent and Trademark Office*

SEQUENCE LISTING

```
<160> NUMBER OF SEQ ID NOS: 14

<210> SEQ ID NO 1
<211> LENGTH: 15
<212> TYPE: PRT
<213> ORGANISM: Homo sapiens

<400> SEQUENCE: 1

Pro Arg His Arg Asp Thr Gly Ile Leu Asp Ser Ile Gly Arg Phe
1               5                   10                  15

<210> SEQ ID NO 2
<211> LENGTH: 17
<212> TYPE: PRT
<213> ORGANISM: Homo sapiens

<400> SEQUENCE: 2

Glu Asn Pro Val Val His Phe Phe Lys Asn Ile Val Thr Pro Arg Thr
1               5                   10                  15
Pro

<210> SEQ ID NO 3
<211> LENGTH: 15
<212> TYPE: PRT
<213> ORGANISM: Homo sapiens

<400> SEQUENCE: 3

Ala Ser Asp Tyr Lys Ser Ala His Lys Gly Phe Lys Gly Val Asp
1               5                   10                  15

<210> SEQ ID NO 4
<211> LENGTH: 15
<212> TYPE: PRT
<213> ORGANISM: Homo sapiens

<400> SEQUENCE: 4

Gly Phe Lys Gly Val Asp Ala Gln Gly Thr Leu Ser Lys Ile Phe
1               5                   10                  15

<210> SEQ ID NO 5
<211> LENGTH: 17
<212> TYPE: PRT
```

<213> ORGANISM: Homo sapiens

<400> SEQUENCE: 5

Glu Asn Pro Val Val His Phe Phe Lys Asn Ile Val Thr Pro Arg Thr
1               5                   10                  15

Pro

<210> SEQ ID NO 6
<211> LENGTH: 15
<212> TYPE: PRT
<213> ORGANISM: Homo sapiens

<400> SEQUENCE: 6

Thr Gln Asp Glu Asn Pro Val Val His Phe Phe Lys Asn Ile Val
1               5                   10                  15

<210> SEQ ID NO 7
<211> LENGTH: 15
<212> TYPE: PRT
<213> ORGANISM: Homo sapiens

<400> SEQUENCE: 7

Gln Asp Glu Asn Pro Val Val His Phe Phe Lys Asn Ile Val Thr
1               5                   10                  15

<210> SEQ ID NO 8
<211> LENGTH: 15
<212> TYPE: PRT
<213> ORGANISM: Homo sapiens

<400> SEQUENCE: 8

Asp Glu Asn Pro Val Val His Phe Phe Lys Asn Ile Val Thr Pro
1               5                   10                  15

<210> SEQ ID NO 9
<211> LENGTH: 15
<212> TYPE: PRT
<213> ORGANISM: Homo sapiens

<400> SEQUENCE: 9

Glu Asn Pro Val Val His Phe Phe Lys Asn Ile Val Thr Pro Arg
1               5                   10                  15

<210> SEQ ID NO 10
<211> LENGTH: 15
<212> TYPE: PRT
<213> ORGANISM: Homo sapiens

<400> SEQUENCE: 10

Met Pro Val Val His Phe Phe Lys Asn Ile Val Thr Pro Arg Thr
1               5                   10                  15

<210> SEQ ID NO 11
<211> LENGTH: 15
<212> TYPE: PRT
<213> ORGANISM: Homo sapiens

<400> SEQUENCE: 11

Arg Ala Ser Asp Tyr Lys Ser Ala His Lys Gly Phe Lys Gly Val
1               5                   10                  15

<210> SEQ ID NO 12
<211> LENGTH: 15
<212> TYPE: PRT
<213> ORGANISM: Homo sapiens

```
<400> SEQUENCE: 12

Ala Ser Asp Tyr Lys Ser Ala His Lys Gly Phe Lys Gly Val Asp
1               5                   10                  15

<210> SEQ ID NO 13
<211> LENGTH: 15
<212> TYPE: PRT
<213> ORGANISM: Homo sapiens

<400> SEQUENCE: 13

Ser Asp Tyr Lys Ser Ala His Lys Gly Phe Lys Gly Val Asp Ala
1               5                   10                  15

<210> SEQ ID NO 14
<211> LENGTH: 15
<212> TYPE: PRT
<213> ORGANISM: Homo sapiens

<400> SEQUENCE: 14

Asp Tyr Lys Ser Ala His Lys Gly Phe Lys Gly Val Asp Ala Gln
1               5                   10                  15
```